United States Patent [19]

Abe et al.

[11] Patent Number: 5,153,176

[45] Date of Patent: Oct. 6, 1992

[54] TRIPEPTIDE DERIVATIVES AND PROTEASE INHIBITOR COMPOSITION COMPRISING THE SAME

[75] Inventors: Yoshihito Abe, Koriyama; Takeshi Nagasawa, Urawa; Katsumasa Kuroiwa; Katsuhiro Yaginuma, both of Koriyama, all of Japan

[73] Assignee: Nitto Boseki Co., Ltd., Fukushima, Japan

[21] Appl. No.: 737,708

[22] Filed: Jul. 30, 1991

[30] Foreign Application Priority Data

Aug. 1, 1990 [JP]  Japan .................... 2-204492

[51] Int. Cl.$^5$ .................. A61K 37/00; C07K 5/00
[52] U.S. Cl. ..................... 514/18; 530/331; 930/10
[58] Field of Search ............ 514/18; 530/330, 331; 930/10

[56] References Cited

U.S. PATENT DOCUMENTS 4,883,863  11/1989  Abe et al. ................ 530/331
5,047,400   9/1991  Vincent et al. ............ 514/18

OTHER PUBLICATIONS

Chou et al., "Prediction of Protein Conformation," Biochemistry, vol. 13, No. 2, 1974.

*Primary Examiner*—Merrell C. Cashion, Jr.
*Assistant Examiner*—B. Celsa
*Attorney, Agent, or Firm*—Darby & Darby

[57] ABSTRACT

Tripeptide derivatives of formula (I) such as N-ε-(p-tosyl)-D-lysyl-L-prolyl-L-argininal have an activity of inhibiting a plurality of trypsin-like serine proteases, e.g., plasmin, thrombin, trypsin, kallikrein, factor Xa, urokinase, etc. in vivo. The tripeptide derivatives can be expected as novel protease inhibitors due to their remarkable pharmaceutical effects.

1 Claim, No Drawings

TRIPEPTIDE DERIVATIVES AND PROTEASE INHIBITOR COMPOSITION COMPRISING THE SAME

BACKGROUND OF THE INVENTION

1. Field of the Invention

The present invention relates to novel tripeptide derivatives and more particularly, to tripeptide derivatives or pharmaceutically acceptable salts thereof which can inhibit a proteases and to protease inhibitor compositions comprising the tripeptide derivatives or salts thereof as an effective ingredient.

2. Statement of the Prior Art

It is well known that a variety of proteases are present in vivo. For example, there are known trypsin-like enzymes such as plasmin, trypsin, kallikrein, thrombin, urokinase, etc.; chymotrypsin-like enzymes; pepsin-like enzymes, etc. These proteases are known to cause various diseases when these enzymes are abnormally activated by some reasons. For example, when a large amount of plasmin formed by abnormal activation is present in blood, a hemorrhagic disease is caused. Plasmin takes part also in inflammation, increases blood permeability of a blood vessel, causes edemata, etc. and develops inflammatory diseases. Accordingly, substances having an inhibitory activity against these proteases are useful as drugs for some clinical treatments and various investigations on these substances have been made heretofore. For example, an anti-plasmin agent is useful as a hemostatic, antiinflammatory and anti-allergic agent; an anti-thrombin agent is useful for the treatment of thrombosis; an anti-trypsin agent is useful for the treatment of pancreatitis; an anti-kallikrein agent is useful for the treatment of inflammation and ulcer; and an anti-urokinase agent is useful for the prevention of hemorrhagic conditions in thrombolytic therapy by urokinase. Protease inhibitors having such activities were thus extensively investigated heretofore. However, the inhibitory activity of these proteases is poor and still insufficient to provide them as drugs for practical use. Any compounds having a sufficient inhibitory activity against several proteases have not been developed so far.

For example, some tripeptide derivatives containing argininal groups are widely known as a protease inhibitor. Acetyl-L-leucyl-L-leucyl-L-argininal (leupeptin) is a compound produced by a certain microorganism (see, e.g., J. Antibiotics (Tokyo), 1969, vol. 22, page 283) but its inhibitory activity is poor (see, e.g., Taisha, 1977, vol. 14, No. 6, page 1087). D-Phenylalanyl-L-prolyl-L-argininal is known as a thrombin inhibitor (e.g., Symposia Biologica Hungarica, 1984, vol. 25, page 277) but its inhibitory activities against other similar trypsin-like enzymes are poor. Furthermore, Umezawa et al. synthesized a number of leupeptin derivatives but any of them has a poor inhibitory activity against a trypsin-like enzyme (see J. Antibiotics (Tokyo), 1988, vol. 41, No. 2, page 220).

SUMMARY OF THE INVENTION

An object of the present invention is to solve these problems in the prior art and develop compounds having an inhibitory activity sufficient for practical use and having a sufficient inhibitory activity also against a plurality of proteases. Another object of the present invention is to develop protease inhibitor compositions comprising the same as an effective ingredient.

The present inventor has made extensive efforts to survey compounds having a more potent inhibitory activity over a broader range than conventional protease inhibitors and as a result, has found that some tripeptide derivatives having a sequence of amino acid residues of D-lysine which has at least one amino group having a certain functional group attached thereto, L-proline and then L-, D- or DL-arginine, and acid addition salts thereof possess an excellent protease inhibitory activity. The present invention has thus been accomplished.

That is, the present invention is concerned with tripeptide derivatives represented by the following general formula (I):

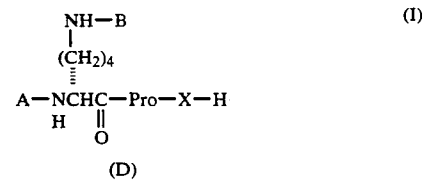

wherein A and B independently represent an arenesulfonyl group (including those substituted with an alkyl group, a halogen atom, an amine derivative residue or an alkyloxy group), an alkanesulfonyl group (including those substituted with an aryl group), an aroyl group (including those substituted with an alkyl group, a halogen atom, an amine derivative residue or an alkyloxy group), an acyl group (including those substituted with an aryl group), a cycloalkanecarbonyl group (including those substituted with an alkyl group, a halogen atom or an amine derivative residue), an alkyloxycarbonyl group (including those substituted with an aryl group, with proviso that a tertiary alkyloxycarbonyl group and an arylmethyloxycarbonyl group are excluded), formyl group, hydrogen atom, adamantyl group, norbornyl group, an alkyl group (including those substituted with an aryl group), an aryl group (including those substituted with an alkyl group) or a nitrogen-containing heterocyclic sulfonyl group (including those substituted with an alkyl group or a halogen atom) (provided that both A and B are not hydrogen simultaneously); Pro represents L-proline residue; and X represents L-, D- or DL-arginine residue; or acid addition salts thereof, and protease inhibitors comprising as the effective ingredient the tripeptide derivatives or pharmaceutically acceptable acid addition salts thereof.

Most of the compounds of the present invention described above potentially inhibit a variety of proteases.

DETAILED DESCRIPTION OF PREFERRED EMBODIMENTS

Preferred examples of the arenesulfonyl group for A and B of formula (I) include benzenesulfonyl, naphthalenesulfonyl; a $C_{1-6}$-alkyl-substituted benzenesulfonyl such as p-toluenesulfonyl, mesitylenesulfonyl, etc. or a $C_{1-6}$-alkyl-substituted naphthalenesulfonyl group; a halogen-substituted benzenesulfonyl such as p-chlorobenzenesulfonyl, etc. or a halogen-substituted naphthalenesulfonyl group; a $C_{2-6}$-alkanoylaminobenzenesulfonyl such as p-acetylaminobenzenesulfonyl, etc. or a $C_{2-6}$-alkanoylaminonaphthalenesulfonyl group; a $C_{1-6}$-alkoxy-substituted benzenesulfonyl such as p- methoxybenzenesulfonyl, etc. or a $C_{1-6}$-alkoxy-substituted naphthalenesulfonyl group. Preferred examples of the alkanesulfonyl group include a $C_{1-6}$-alkanesulfonyl group, e.g., methanesulfonyl, ethanesulfonyl, propanesulfonyl, butanesulfonyl, etc.; or a phenyl-substituted $C_{1-6}$-alkanesulfonyl group, e.g., phenylmethanesulfonyl, etc. Preferred examples of the aroyl group include benzoyl, naphthoyl; a $C_{1-6}$-alkylsubstituted benzoyl such as toluoyl, p-ethylbenzoyl, etc. or a $C_{1-6}$-alkyl-substituted naphthoyl group; a halogen-substituted benzoyl such as p-chlorobenzoyl, etc., or a halogen-substituted naphthoyl group. Preferred examples of the acyl group include a $C_{2-10}$-acyl group such as acetyl, propionyl, octanoyl, etc.; and a phenyl-substituted containing heterocyclic sulfonyl group include quinolinesulfonyl, pyridinesulfonyl, etc.

As X in general formula (I), L-arginine residue is preferred.

The tripeptide derivatives represented by general formula (I) and their acid addition salts of the present invention may be prepared by various processes. The processes are described below but synthesis of the compounds represented by general formula (I) and their acid addition salts is not limited to the processes shown below.

The tripeptide derivatives of formula (I) and their acid addition salts may be synthesized according to Reaction Schemes 1 and 2.

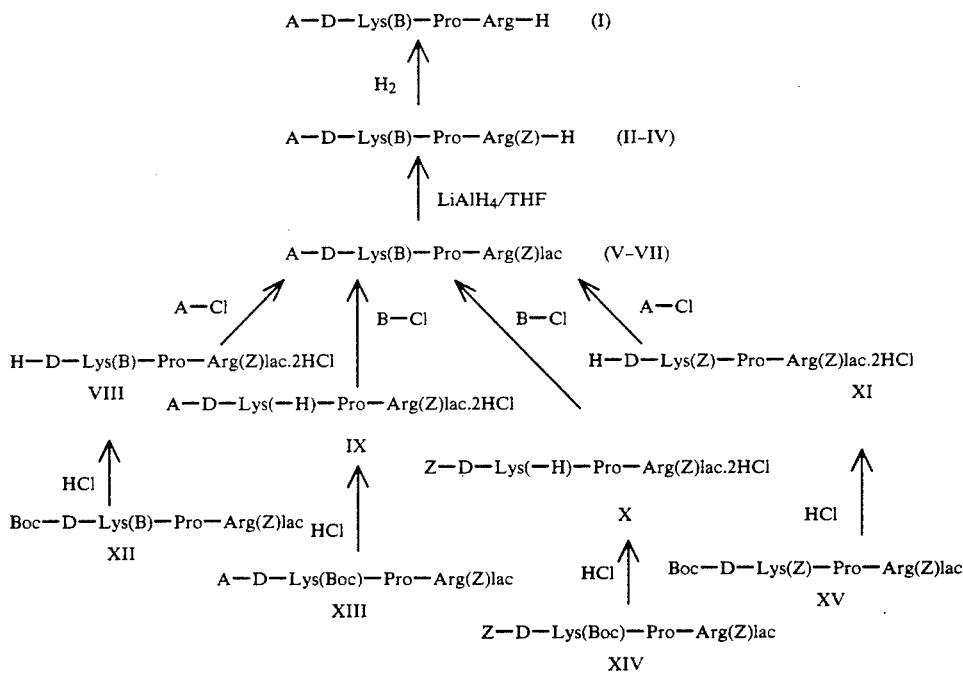

In Reaction Scheme 1:

I     I': A, B = substituent
      I'': A = H, B = substituent
      I: A = substituent, B = H II-IV   II: A, B = substituent
       III: A = Z, B = substituent
       IV: A = substituent, B = Z V-VII   V: A, B = substituent
       VI: A = Z, B = substituent
       VII: A = substituent, B = Z stituted $C_{2-10}$-acyl group such as phenylacetyl, etc. Preferred examples of the cycloalkanecarbonyl group include a $C_{5-7}$-cycloalkanecarbonyl group such as cyclopentanecarbonyl, cyclohexanecarbonyl, etc.; and an amino-$C_{1-6}$-alkylsubstituted $C_{5-7}$-cycloalkanecarbonyl group such as 4-(aminomethyl)cyclohexanecarbonyl, etc. Preferred examples of the alkyloxycarbonyl include a $C_{1-6}$-alkyloxycarbonyl group such as methoxycarbonyl, ethoxycarbonyl, propoxycarbonyl, butoxycarbonyl, pentoxycarbonyl, hexoxycarbonyl, etc. Preferred examples of the alkyl group include a $C_{1-10}$-alkyl group such as methyl, ethyl, propyl, etc.; or a phenyl-substituted $C_{1-10}$-alkyl group such as benzyl, phenethyl, etc. Preferred examples of the aryl group include phenyl or naphthyl. Preferred examples of the nitrogen-

REACTION SCHEME 2

| | |
|---|---|
| A—D—Lys(B)—Pro—Arg(Z)lac | (V, VI, VII, XII, XIII, XIV, XV) |
| H—Arg(Z)lac.2HCl | |
| MA method | |
| | XVI: A, B = substituent |
| | XVII: A = Z, B = substituent |
| A—D—Lys(B)—Pro—OH | XVIII: A = substituent, B = Z |
| XVI-XXII | XIX: A = Boc, B = substituent |
| | XX: A = substituent, B = Boc |
| | XXI: A = Z, B = Boc |
| H—Pro—OH | XXII: A = Boc, B = Z |
| A—D—Lys(B)—SDP | |
| H—SDP | |
| DCC | |
| | XXIII: A, B = substituent |
| | XXIV: A = Z, B = substituent |

-continued

| | |
|---|---|
| A—D—Lys(B)—OH | XXV: A = substituent, B = Z |
| XXIII-XXIX | XXVI: A = Boc, B = substituent |
| | XXVII: A = substituent, B = Boc |
| | XXVIII: A = Z, B = Boc |
| | XXIV: A = Boc, B = Z |

Abbreviations used in Scheme 1 and 2 are as follows:

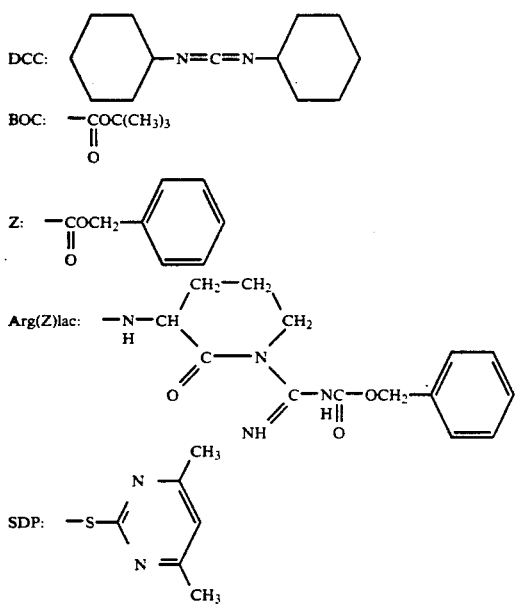

Among the tripeptide derivatives of formula (I), N-α-N-ε-di-substituted-D-lysyl-L-prolyl-argininal (I') wherein A and B are both substituents, not hydrogen, N-α-H-N-ε-substituted-D-lysyl-L-prolylargininal (I") wherein A is hydrogen atom and B is a substituent, and N-α-substituted-N-ε-H-D-lysyl-L-prolyl-argininal (I) wherein A is a substituent and B is hydrogen are prepared by catalytically hydrogenating N-α-N-ε-di-substituted-D-lysyl-L-prolyl-N-G-benzyloxycarbonyl-argininal (II), N-α-benzyloxycarbonyl-N-ε-substituted-D-lysyl-L-prolyl-N-ε-benzyloxycarbonylargininal (III) or N-α-substituted-N-ε-benzyloxycarbonyl-D-lysyl-L-prolyl-N-G-benzyloxycarbonylargininal (IV), respectively, in the presence of an acid to remove the benzyloxycarbonyl protective group. Herein, in the case of using, e.g., hydrochloric acid as the acid, the tripeptide derivatives of (I'), (I") and (I) are obtained as the hydrochlorides, and in the case of using sulfuric acid, the tripeptide derivatives are obtained as the sulfates. Other acid addition salts may be obtained in a similar manner.

The tripeptide aldehyde derivatives (II), (III) and (IV) protected with benzyloxycarbonyl may be synthesized by reducing the corresponding tripeptide lactam derivatives, i.e., N-α-N-ε-di-substituted-D-lysyl-L-prolyl-N-G-benzyloxycarbonyl-arginine-67-lactam (V), N-α-benzyloxycarbonyl-N-ε-substituted-D-lysyl-L-prolyl-N-G-benzyloxycarbonyl-arginine-67-lactam (VI) and N-α-substituted-N-ε-benzyloxycarbonyl-D-lysyl-L-proyl-arginine-67-lactam (VII) with lithium aluminum hydride in tetrahydrofuran (THF), respectively. The tripeptide lactam derivatives (V), (VI) and (VII) can be prepared by reacting N-α- or N-ε-substituted-D-lysyl-L-prolyl-N-G-benzyloxycarbonyl-arginine-δ-lactam hydrochloride (VIII) or (IX); N-α-benzyloxycarbonyl-D-lysyl-L-prolyl-N-G-benzyloxycarbonyl-arginine-δ-lactam hydrochloride (X); and N-ε-benzyloxycarbonyl-D-lysyl-L-proyl-N-G-benzyloxycarbonyl-arginine-δ-lactam hydrochloride (XI) with the corresponding substituted chloride A-Cl or B-Cl (e.g., p-toluenesulfonyl chloride), respectively. The monosubstituted or unsubstituted tripeptide lactam derivatives (VIII), (IX), (X) and (XI) may be obtained by treating the corresponding t-butoxycarbonyl-containing compounds, i.e., N-α-(t-butoxycarbonyl)-N-ε-substituted-D-lysyl-L-prolyl-N-G-benzyloxycarbonyl-arginine-δ-lactam (XII); N-α-substituted-N-ε-(t-butoxycarbonyl)-D-lysyl-L-prolyl-N-G-benzyloxycarbonyl-arginine-δ-lactam (XIII); N-ε-benzyloxycarbonyl-N-ε-(t-butoxycarbonyl)-D-lysyl-L-prolyl-N-G-benzyloxycarbonyl-arginine-δ-lactam (XIV); and N-α-(t-butoxycarbonyl)-N-ε-benzyloxycarbonyl-L-prolyl-N-G-benzyloxycarbonyl-arginine-δ-lactam (XV), respectively, with, e.g., an acetic acid solution containing 2 N hydrogen chloride.

The tripeptide lactam derivatives (V), (VI), (VII), (XII), (XIII), (XIV) and (XV) may be synthesized by processes known in the peptide chemistry, as illustrated in Reaction Scheme 2 (see, e.g., Nobuo Izumiya et al., "Basic and Experimental Synthesis of Peptide", Maruzen Publishing Co.). That is, these tripeptide lactam derivatives may be obtained by condensing N-G-benzyloxycarbonyl-arginine-δ-lactam hydrochloride with N-α-N-ε-di-substituted-D-lysyl-L-proline (XVI); N-α-benzyloxycarbonyl-N-ε-substituted-D-lysyl-L-proline (XVII); N-α-substituted-N-ε-benzyloxycarbonyl-D-lysyl-L-proline (XVIII); N-α-(t-butoxycarbonyl)-N-ε-substituted-D-lysyl-L-proline (XIX); N-α-substituted-N-ε-(t-butoxycarbonyl)-D-lysyl-L-proline (XX); N-α-benzyloxycarbonyl-N-ε-(t-butoxycarbonyl)-D-lysyl-L-proline (XXI); and N-α-(t-butoxycarbonyl)-N-ε -benzyloxycarbonyl-D-lysyl-L-proline (XXII); respectively, according to, e.g., the mixed anhydride method (MA method). The dipeptide derivatives (XVI), (XVII), (XVIII), (XIX), (XX), (XXI) and (XXII) may be obtained by condensation of activated esters (e.g., 4,6-dimethylpyrimidin-2-yl-thiol ester) of N-α-N-ε-di-substituted-D-lysine (XXIII); N-α-benzyloxycarbonyl-N-ε-substituted-D-lysine (XXIV); N-α-substituted-N-ε-benzyloxycarbonyl-D-lysine (XXV); N-α-(t-butoxycarbonyl)-N-ε-substituted-D-lysine (XXVI); N-α-substituted-N-ε-(t-butoxycarbonyl)-D-lysine (XXVII); N-α-benzyloxycarbonyl-N-ε-(t-butoxycarbonyl)-D-lysine (XXVIII); and N-α-(t-butoxycarbonyl)-N-ε-(benzyloxycarbonyl)-D-lysine (XXIX); with proline, respectively, by known methods in the peptide chemistry.

In the processes described above, the final products of the tripeptide derivatives may, in some cases, contain a small amount of the products having D-argininal residue. However, these products do not affect their therapeutic application.

The acid addition salts of the tripeptide derivatives of formula (I) may be used as drugs like the tripeptide derivatives for the therapeutic purpose and are preferably acceptable pharmacologically and medically. However, the basis for the activity resides in the tripeptide derivatives themselves which are the basic moiety but the acid moiety is not so important. Nevertheless, a difference in the acid moiety results in differences in the easiness of isolation, stability and solubility of compound. Examples of suitable acid addition salts of the tripeptide derivatives of formula (I) include inorganic acid salts such as hydrochlorides, hydrobromides, sulfates, etc.; organic carboxylates such as acetates, oxalates, succinates, malates, citrates, lactates, etc.; organic sulfonates such as benzenesulfonates, paratoluenesulfonates, methanesulfonates, etc. Salts which are pharmaceutically difficultly acceptable (e.g., hydrofluorides and perchlorates) and pharmaceutically non-acceptable salts may be utilized for the isolation of the pharmaceutically acceptable salts or for the purification of bases; alternatively, these salts are useful and valuable for preparing the pharmaceutically acceptable salts by methods well known to one skilled in the art. In the case of the tripeptide derivatives having a plurality of free amino groups, the tripeptide derivatives may be used in the form of mono- or poly-acid addition salts or in the form of mixed acid addition salts with a plurality of acids.

It has been confirmed that when a protease activity of the tripeptide derivatives and their acid addition salts of the present invention is determined in the presence of a trypsin-like serine protease such as plasmin, thrombin, trypsin, kallikrein, factor Xa, urokinase, etc., the compounds of the present invention all have a high inhibitory activity against each enzyme.

Accordingly, the protease inhibitor composition comprising as the effective ingredient the tripeptide derivative of formula (I) or its pharmaceutically acceptable acid addition salt is useful for the treatment of diseases associated with a trypsin-like serine protease, for example, inflammation, hemorrhage, allergy, pancreatitis and ulcer.

Where the compound of the present invention is used as a drug, its application is not strictly limited. The compound may be prepared into a suitable medical preparation conventionally used in the pharmaceutical field and used by intravenous injection, intramuscular injection, drop transfusion, oral administration, etc. Daily dose is suitably 1 to 1000 mg per adult and needless to say, the dose may be appropriately varied, if necessary.

EXAMPLES

Hereafter the present invention is explained by referring to specific examples. In EXAMPLES, conventional abbreviations shown below are used.

M=molar concentration, N=normal concentration, g=gram, mg=milligram, l=liter, ml=milliliter, dec.-=decomposed, mmol=millimol, TLC=thin layer chromatography, mp=melting point, mM=millimolar concentration, Rf=relative mobility, p-tosyl=p-toluenesulfonyl, DCC=dicyclohexylcarbodiimide, $NaHCO_3$=sodium hydrogencarbonate, $MgSO_4$=magnesium sulfate, THF=tetrahydrofuran, DMF=dimethylformamide, $LiAlH$=lithium aluminum hydride, CHA=3-carboxy-4-hydroxyanilide, pNA=paranitroanilide.

In TLC, silica gel $F_{254}$ plate (manufactured by Merck) used and the following solvents were used.

| | |
|---|---|
| $Rf_1$ = | chloroform:methanol:acetic acid: water (80:20:2.5:5) |
| $Rf_2$ = | chloroform:methanol (20:1) |
| $Rf_3$ = | chloroform:methanol (5:1) |
| $Rf_4$ = | ethyl acetate:pyridine:acetic acid: water (30:20:6:11) |
| $Rf_5$ = | chloroform:methanol (10:1) |
| $Rf_6$ = | ethyl acetate:pyridine:acetic acid: water (20:20:6:11) |
| $Rf_7$ = | ethyl acetate:pyridine:acetic acid: water (60:20:6:11) |

EXAMPLE 1

Synthesis of N-ε-(p-tosyl)-D-lysyl-L-prolyl-L-argininal sulfate a)
N-α-Benzyloxycarbonyl-N-ε-(p-tosyl)-D-lysyl-L-proline A suspension of N-α-benzyloxycarbonyl-N-ε-(p-tosyl)-D-lysine (81.3 g, 188 mmol, described in Collection Czech. Chem. Commun., 1967, vol. 32, page 1242), 2-mercapto-4,6-dimethylpyrimidine (31.6 g, 225 mmol) and ethyl acetate (260 ml) was cooled to 0° to 5° C. A solution of DCC (38.7 g, 188 mmol) in ethyl acetate (110 ml) was gradually added to the suspension. At this step, the reaction solution was kept at 0° to 5° C. The mixture was stirred overnight at room temperature. The precipitated crystals were filtered out and the filtrate was washed with 10% $NaHCO_3$ aqueous solution and then with sodium chloride aqueous solution. After drying over $MgSO_4$, the filtrate was concentrated to give 102.5 g (98%) of N-α-benzyloxycarbonyl-N-ε-(p-tosyl)-D-lysine-4,6-dimethylpyrimidin-2-ylthiol ester.

This activated ester (102.5 g, 185 mmol) was dissolved in THF (380 ml). The activated ester solution in THF was added to a suspension of L-proline (21.2 g, 185 mmol) and triethylamine (37.3 g, 368 mmol) in water (200 ml) at room temperature followed by stirring overnight. The reaction solution was concentrated to a volume of about ⅓ with an evaporator. After water was added to the concentrate, the mixture was washed twice with ether. A pH of the aqueous layer was adjusted to 2 with 5 N hydrochloric acid under cooling at 0° C. After extracting with ethyl acetate, the organic layer was washed twice with chilled 5% hydrochloric acid and twice with saturated sodium chloride aqueous solution. After drying over $MgSO_4$, an excess of the solvent was distilled off and the residue was crystallized from ethyl acetate hexane to give 48.0 g (70%) of the title compound.

TLC = $Rf_1$ = 0.37–0.52    mp: 154–155° C.
$[\alpha]_D^{24}$ = 23.5° (C = 0.5, DMF)

b)
N-α-Benzyloxycarbonyl-N-ε-(p-tosyl)-D-lysyl-L-prolyl-N-G-benzyloxycarbonyl-L-arginine-δ-lactam After ethyl acetate (90.8 ml, 363 mmol) containing 4 N hydrogen chloride was added to a solution of N-α-(t-butoxycarbonyl)-N-G-benzyloxycarbonyl-L-arginine-δ-lactam (12.9 g, 33 mmol) in chloroform (33 ml), the mixture was stirred at room temperature for 3 hours. Dry ether (50 ml) was added to the reaction mixture. The precipitated crystals were taken by filtration and dried to give 10.9 g (91%) of N-G-benzyloxycarbonyl-L-arginine-δ-lactam hydrochloride.

Triethylamine (8.4 ml, 60 mmol) was added to a solution of the crystals (10.9 g, 30 mmol) in DMF (45 ml) at −10° C. The resulting suspension was added to the mixed acid anhydride prepared below.

N-α-Benzyloxycarbonyl-N-ε-(p-tosyl)-D-lysyl-L-proline (15.9 g, 30 mmol) was dissolved in DMF (36 ml) and the solution was cooled to −15° C. Then, N-methylmorpholine (3.30 ml, 30 mmol) and isobutyl chloroformate (3.89 ml, 30 mmol) were added, in sequence, to the solution. After completion of the addition, stirring was continued for 10 minutes. Thereafter, the suspension of the arginine-δ-lactam derivative suspension in DMF was added to the mixed acid anhydride obtained. The reaction mixture was reacted at −10° C. for 30 minutes and at 0° C. for 30 minutes. After DMF was distilled off under reduced pressure, ethyl acetate was added to the residue. The mixture was washed, in sequence, with 5% hydrochloric acid aqueous solution, saturated sodium chloride aqueous solution, 10% NaHCO$_3$ aqueous solution and saturated sodium chloride aqueous solution. After drying over MgSO$_4$, the residue was subjected to silica gel column chromatography and 12.2 g (51%) of the title compound was obtained as an oil from the fraction eluted with chloroform-methanol.

TLC=Rf$_2$=0.31−0.39.

$[α]_D^{24}$= −41° (C=0.5).

Elemental analysis as C$_{40}$H$_{49}$N$_7$O$_9$.3/2H$_2$O: Calcd.: C 57.81%, H 6.30%, N 11.79%; Found: C 57.60%, H 6.01%, N 11.42%.

c)
N-α-Benzyloxycarbonyl-N-ε-(p-tosyl)-D-lysyl-L-prolyl-N-G-benzyloxycarbonyl-L-argininal A solution of N-α-benzyloxycarbonyl-N-ε-(p-toxyl)-D-lysyl-L-prolyl-N-G-benzyloxycarbonyl-L-arginine-δ-lactam (10.1 g, 12.5 mmol) in THF (63 ml) was stirred under cooling at −30° C. To the solution was dropwise added a 0.4 M LiAlH$_4$ solution in dry THF (32 ml). In this case, a dropping rate was controlled so as not to exceed −30° C. After the dropwise addition, the mixture was stirred for an hour at −30 to −20° C. After completion of the reaction, a pH of the mixture was adjusted to 2 with 1 N sulfuric acid aqueous solution and water was then added thereto until it became turbid. Thereafter, the reaction mixture was washed with hexane. After the aqueous layer was extracted with chloroform, the organic layer was washed with water. After drying over MgSO$_4$, the extract was concentrated and dried under reduced pressure to give 6.3 g (60%) of the title compound.

TLC=Rf$_3$=0.42−0.47.

$[α]_D^{24}$= −21° (C=0.5, DMF).

Elemental analysis as C$_{40}$H$_{51}$N$_7$O$_9$S.3/2H$_2$O: Calcd.: C 57.67%, H 6.53%, N 11.77%; Found: C 57.89%, H 6.28%, N 11.61%.

d) N-ε-(p-Tosyl)-D-lysyl-L-prolyl-L-argininal sulfate

A suspension of 1 N sulfuric acid aqueous solution (10.45 ml) of N-α-benzyloxycarbonyl-N-ε-(p-tosyl)-D-lysyl-L-prolyl-N-G-benzyloxycarbonyl-L-argininal (4.43 g, 5.50 mmol), 85% aqueous methanol (400 ml) and palladium black (2.0 g) was stirred at room temperature in a hydrogen atmosphere. After disappearance of the starting materials was confirmed by TLC, palladium black was filtered off and the filtrate was concentrated. The residue was dissolved in a small amount of methanol. Ether was added to the solution followed by recrystallization. The precipitated crystals were taken by filtration. After drying under reduced pressure, 2.76 g (79%) of the title compound was obtained.

TLC=Rf$_4$=0.48−0.66 mp: 115°-140° C.

$[α]_D^{20}$= −19° (C=0.25, DMF).

Elemental analysis as C$_{24}$H$_{41}$N$_7$O$_9$S$_2$.2H$_2$O: Calcd.: C 42.91%, H 6.75%, N 14.60%; Found: C 43.01%, H 6.68%, N 14.38%

EXAMPLE 2

Synthesis of N-ε-(p-tosyl)-D-lysyl-L-prolyl-L-argininal dihydrochloride

N-α-Benzyloxycarbonyl-N-ε-(p-tosyl)-D-lysyl-L-prolyl-N-G-benzyloxycarbonyl-L-argininal (0.74 g, 0.92 mmol), 1 N hydrochloric acid aqueous solution (0.92 ml), 85% methanol (150 ml) and palladium black (1.0 g) were used and treated in a manner similar to Example 1 a) to give 0.47 g (84%) of the title compound.

TLC=Rf$_4$=0.48−0.67 mp: 145° C. (dec.).

$[α]_{20}^{20}$= −65° (C=0.5, DMF).

Elemental analysis as C$_{24}$H$_{39}$N$_7$O$_5$S.7/4Hcl; Calcd.: 48.07%, H 6.84%, N 16.35%; Found: 48.30%, H 6.81%, N 16.32%.

EXAMPLE 3

Synthesis of N-ε-(2-naphthalenesulfonyl)-D-lysyl-L-prolyl-L-argininal sulfate a)
N-α-Benzyloxycarbonyl-N-ε-(t-butoxycarbonyl)-D-lysyl L-proline N-α-Benzyloxycarbonyl-N-ε-(t-butoxycarbonyl)-D-lysine (22.8 g, 60 mmol), a suspension of 2-mercapto-4,6-dimethylpyrimidine (10.1 g, 72 mmol) in ethyl acetate (110 ml) and a solution of DCC (12.4 g, 60 mmol) in ethyl acetate (260 ml) were treated in a manner similar to Example 1 a) to synthesize the activated ester.

A solution of the obtained activated ester, N-α-benzyloxycarbonyl-N-ε-(t-butoxycarbonyl)-D-lysine-4,6-dimethylpyrimidin-2-ylthiol ester (29.2 g, 58 mmol) in THF (76 ml), L-proline (7.4 g, 64 mmol) and triethylamine (14.7 ml, 104 mmol) were treated by the coupling method shown in Example 1 a) to give 23.5 g (84%) of N-α-benzyloxycarbonyl-N-ε-(t-butoxycarbonyl)-D-lysyl-L-proline as an oil.

TLC=Rf$_1$=0.53−0.62.

b)
N-α-Benzyloxycarbonyl-N-ε-(t-butoxycarbonyl)-D-lysyl-L-prolyl-N-G-benzyloxycarbonyl-L-arginine-δ-lactam N-α-(t-Butoxycarbonyl)-N-G-benzyloxycarbonyl-L-arginine-δ-lactam (17.5 g, 45 mmol), chloroform (45 ml), ethyl acetate solution (67.5 ml, 270 mmol) containing 4 N hydrogen chloride, dry ether (100 ml), N-α-benzyloxycarbonyl-N-ε-(t-butoxycarbonyl)-D-lysyl-L-proline (4.95 g, 45 mmol), 50 ml each of DMF, triethylamine (12.6 ml, 90 mmol), N-methylmorpholine (49.5 ml, 45 mmol) and isobutyl chloroformate (5.84 ml, 45 mmol) were used and treated in a manner similar to Example 1 b) to give 19.4 g (51%) of the title compound as an oil.

TLC=Rf$_2$=0.20-0.28.

$[α]_D^{20}$= −41 ° (C=0.5, DMF).

Elemental analysis as C$_{38}$H$_{51}$N$_7$O$_9$.2H$_2$O: Calcd.: C 57.65%, H 6.68%, N 12.31%;

Found: C 58.06%, H 7.05%, N 12.47%.

c)
N-α-Benzyloxycarbonyl-D-lysyl-L-prolyl-N-G-benzyloxycarbonyl-L-arginine-δ-lactam hydrochloride After N-α-benzyloxycarbonyl-N-ε-(t-butoxycarbonyl)-D-lysyl-L-prolyl-N-G-benzyloxycarbonyl-L- arginine-δ-lactam (19.2 g, 25.6 mmol) was dissolved in a solution of acetic acid (64 ml, 128 mmol) containing 2 N hydrogen chloride, the solution was sitrred at room temperature for 2 hours. The reaction mixture was poured onto dry ether (1 l) and the precipitated crystals were taken by filtration.

Yield, 17.0 g (92%).
TLC=Rfl=0.24–0.29.

d)

N-α-Benzyloxycarbonyl-N-ε-(2-naphthalenesulfonyl)-D-lysyl-L-prolyl-N-G-benzyloxycarbonyl-L-arginine-δ-lactam N-α-Benzyloxycarbonyl-D-lysyl-L-prolyl-N-Gbenzyloxycarbonyl-L-arginine-δ-lactam dihydrochloride (1.81 g, 2.5 mmol) was dissolved in chloroform (70 ml). To the solution were added 30% (w/w) potassium carbonate aqueous solution (6 ml) and 2-naphthalenesulfonyl chloride (0.62 g, 2.75 ml). The mixture was vigorously stirred for 20 minutes using a separating funnel. After allowing to stand overnight, the aqueous layer was removed and the organic layer was further washed with water. After drying over MgSO$_4$, the solvent was distilled off under reduced pressure. The residue was subjected to silica gel column chromatography. Elution with chloroform-methanol gave 1.29 g (61%) of the title compound as an oil.

$[\alpha]_D^{24} = -49°$ (C=0.25, DMF).
TLC=Rf$_2$=0.30–0.39.

Elemental analysis as C$_{43}$H$_{49}$N$_7$O$_9$S.2H$_2$O: Calcd.: C 58.95%, H 6.09%, N 11.19%; Found : C 59.14%, H 5.69%, N 10.84%.

e)

N-α-Benzyloxycarbonyl-N-ε-(2-naphthalenesulfonyl)-D-lysyl-L-prolyl-N-G-benzyloxycarbonyl-L-argininal A solution of N-o-benzyloxycarbonyl-N-α-(2-naphthalenesulfonyl)-D-lysyl-L-prolyl-N-G-benzyloxycarbonyl-L-arginine-δ-lactam (0.92 g, 1.10 mmol) in dry THF (6 ml) and a 0.4 M LiAlH$_4$ solution in dry THF (2.75 ml, 1.10 mmol) were used and treated in a manner similar to Example 1 c) to give 0.56 g (60%) of the title compound as an oil.

TLC=Rf$_5$=0.23–0.32.
$[\alpha]_D^{20} = -7°$ (C=0.15, DMF).

f)

N-ε-(2-Naphthalenesulfonyl)-D-lysyl-L-prolyl-L-argininal sulfate

N-α-Benzyloxycarbonyl-N-ε-(2-naphthalenesulfonyl)-D-lysyl-L-prolyl-N-G-benzyloxycarbonyl-L-argini nal (0.45 g, 0.54 mmol), 1 N sulfuric acid (0.94 ml, 0.94 mmol), 85% methanol (150 ml) and palladium black (1.0 g) were used and treated in a manner similar to Example 1 d) to give 0.20 g (66%) of the title compound as crystals.

TLC=Rf$_4$=0.56–0.72 mp: 118° C. (dec.).
$[\alpha]_D^{20} = -24°$ (C=0.5, DMF).
Elemental analysis as C$_{27}$H$_{41}$N$_7$O$_9$S$_2$.3/2H$_2$O:
Calcd.: C 46.40%, H 6.35%, N 14.03%;
Found: C 46.62%, H 6.02%, N 13.41%.

EXAMPLE 4

Synthesis of N-ε-(8-quinolinesulfonyl)-D-lysyl-L-prolyl-L-argininal sulfate a)

N-α-Benzyloxycarbonyl-N-ε-(8-quinolinesulfonyl)-D-lysyl-L-prolyl-N-G-benzyloxycarbonyl-L-arginine-δ-lactam 8-Quinolinesulfonyl chloride (0.63 g, 2.75 mmol) was used instead of 2-naphthalenesulfonyl chloride and treated in a manner similar to Example 3 d) to give 1.03 g (49%) of the title compound as an oil.

TLC=Rf$_5$=0.49–0.55.
$[\alpha]_D^{24} = -44°$ (C=0.25, DMF).

b)

N-α-Benzyloxycarbonyl-N-ε-(8-quinolinesulfonyl)-D-lysyl-L-prolyl-N-G-benzyloxycarbonyl-L-argininal A solution of N-α-benzyloxycarbonyl-N-ε-(8-quinolinesulfonyl)-D-lysyl-L-prolyl-N-G-benzyloxycarbonyl-L-arginine-δlactam (0.96 g, 1.14 mmol) in dry THF (6 ml) and a 0.4 M LiAlH$_4$ solution in dry THF (2.85 ml, 1.14 mmol) were used and treated in a manner similar to Example 1 c) to give 0.43 g (45%) of the title compound as an oil.

TLC=Rf$_5$=0.23–0.32.
$[\alpha]_D^{20} = -7°$ (C=0.15, DMF).
Elemental analysis as C$_{42}$H$_{50}$N$_8$O$_9$S.H$_2$O: Calcd.: C 58.63%, H 6.09%, N 13.03%; Found: C 58.49%, H 5.97%, N 12.82%.

c)

N-ε-(8-Quinolinesulfonyl)-D-lysyl-L-prolyl-L-argininal sulfate

N-α-Benzyloxycarbonyl-N-ε-(8-quinolinesulfonyl)-D-lysyl-L-prolyl-N-G-benzyloxycarbonylL-argininal (0.37 g, 0.44 mmol), 1 N sulfuric acid (0.80 ml, 0.80 mmol), 85% methanol (150 ml) and palladium black (1.0 g) were used and treated in a manner similar to Example 1 d) to give 0.16 g (54%) of the title compound as crystals.

TLC=Rf$_4$=0.53–0.70 mp: 142° C. (dec.).
$[\alpha]_D^{20} = -28°$ (C=0.5, DMF)
Elemental analysis as C$_{26}$H$_{40}$N$_8$O$_9$S$_2$.2H$_2$O: Calcd.: C 44.06%, H 6.26%, N 15.81%; Found: C 44.38%, H 6.36%, N 15.99%.

EXAMPLE 5

Synthesis of N-α-ethanesulfonyl-D-lysyl-L-prolyl-L-argininal sulfate a)

N-α-Benzyloxycarbonyl-N-ε-ethanesulfonyl-D-lysyl-L-prolyl-N-G-benzyloxycarbonyl-L-arginine-δ-lactam N-α-Benzyloxycarbonyl-D-lysyl-L-prolyl-N-G-benzyloxycarbonyl-L-arginine-δ-lactam (1.81 g, 2.5 mmol) was dissolved in chloroform (50 ml). After 30 % (w/w) potassium carbonate aqueous solution (6 ml) was added to the solution, the mixture was vigorously shaken for an hour using a separating funnel, while adding ethanesulfonyl chloride (0.78 ml, 8.25 mmol) to the mixture in 3 portions. After allowing to stand overnight, the aqueous layer was removed and the organic layer was washed with water. After drying over MgSO$_4$, the solvent was distilled off under reduced pressure and the residue was subjected to silica gel column chromatography. Elution with a solvent mixture of chloroform-methanol gave 1.15 g (62%) of the desired title compound as an oil.

TLC=Rf$_5$=0.46–0.54, b)
N-α-Benzyloxy-N-ε-ethanesulfonyl-D-lysyl-L-prolyl-N-G-benzyloxycarbonyl-L-argininal A solution of N-α-benzyloxycarbonyl-N-ε-ethanesulfonyl-D-lysyl-L-prolyl-N-G-benzyloxycarbonyl-L-arginine-δ-lactam (1.10 g, 1.48 mmol) in dry THF (6 ml) and a 0.4 M LiAlH$_4$ solution in dry THF (2.85 ml, 1.14 mmol) were used and treated in a manner similar to Example 1 c) to give 0.17 g (15%) of the title compound as an oil.

TLC=Rf$_5$=0.14–0.24.
$[\alpha]_D^{20}$= −20° (C=0.15, DMF).

c) N-ε-Ethanesulfonyl-D-lysyl-L-prolyl-L-argininal sulfate

N-α-Benzyloxycarbonyl-N-ε-ethanesulfonyl-D-lysyl-L-prolyl-N-G-benzyloxycarbonyl-L argininal (0.17 g, 0.23 mmol), 1 N sulfuric acid aqueous solution (0.40 ml, 0.40 mmol), methanol (150 ml) and palladium black (1.0 g) were used and treated in a manner similar to Example 1 d) to give 0.14 g (100%) of the title compound.

TLC=Rf$_4$=0.28–0.44; mp: 150° C. (dec.).
$[\alpha]_D^{20}$= −42° (C=0.15, H$_2$O).

Elemental analysis as C$_{19}$H$_{39}$N$_7$O$_9$S$_2$.3/2H$_2$O; Calcd.: C 37.99%, H 7.05%, N 16.32%; Found: C 37.86%, H 7.11%, N 16.07%,

EXAMPLE 6

Synthesis of N-ε-benzoyl-D-lysyl-L-prolylL-argininal sulfate a)
N-α-Benzylo,xycarbonyl-N-ε-benzoyl-D-lysyl-L-proline A suspension of N-α-benzyloxycarbonyl-N-ε-benzoyl-D-lysine (2.70 g, 7.02 mmol), 2-mercapto-4,6-dimethylpyrimidine (1.18 g, 8.42 mmol) and ethyl acetate (40 ml) was cooled to 0°–5° C. DDC (1.45 g, 7.02 mmol) was added to the suspension and the mixture was stirred overnight at room temperature. The precipitated qrystals were filtered and the filtrate was washed with 10% NaHCO$_3$ aqueous solution and then with sodium chloride aqueous solution. After drying over MgSO$_4$, the drying agent was removed and concentrated to give 3.44 g (97%) of N-α-benzyloxycarbonyl-N-ε-benzoyl-D-lysine-4,6-dimethylpyrimidin-2-ylthiol ester.

This activated ester (3.44 g, 6.79 mmol) was dissolved in THF (8.8 ml). The activated ester solution in THF was added to a suspension of L-proline (0.86 g, 7.47 mmol) and triethylamine (1.71 ml, 12.2 mmol) in water (8.8 ml) at room temperature followed by stirring overnight. The reaction solution was concentrated to a volume of about ⅓ with an evaporator. After water (10 ml) was added to the concentrate, the mixture was washed twice with ether (5 ml). A pH of the aqueous layer was adjusted to 2 with 5 N hydrochloric acid under cooling at 0° C. After extracting with ethyl acetate, the organic layer was washed twice with chilled 5% hydrochloric acid and twice with saturated sodium chloride aqueous solution. After drying over MgSO$_4$, an excess of the solvent was distilled off and the residue was crystallized from ethyl acetate-hexane to give 2.85 g (87%) of the title compound.

TLC=Rf$_1$=0.54–0.62; mp: 66°–68° C.
$[\alpha]_D^{20}$= −16° (C=0.25, DMF).

b)
N-α-Benzyloxycarbonyl-N-ε-benzoyl-D-lysyl-L-prolyl-N-G-benzyloxycarbonyl-L-arginine-δ-lactam After N-α-(t-butoxycarbonyl)-N-G-benzyloxycarbonyl-L-arginine-δ-lactam (2.21 g, 5.65 mmol) was dissolved in chloroform (6 ml), ethyl acetate (8.5 ml, 33.9 mmol) containing 4 N hydrogen chloride was added to the solution. The mixture was stirred for 2 hours. Ether (15 ml) was added to the reaction mixture. The precipitated crystals were taken by filtration and dried with a vacuum pump.

The crystals were dissolved in DMF (6 ml). After cooling to −10° C., triethylamine (1.58 ml, 11.3 mmol) was added to the solution. The resulting suspension was added to the mixed acid anhydride prepared below.

N-α-Benzyloxycarbonyl-N-s-benzoyl-D-lysyl-L-proline (2.70 g, 5.65 mmol) was dissolved in DMF (6 ml) and the solution was cooled to −15° C. Then, N-methylmorpholine (0.62 ml, 5.65 mmol) and isobutyl chloroformate (0.73 ml, 5.65 mmol) were added at the same temperature, in sequence, to the solution. After completion of the addition, stirring was continued for 10 minutes. Thereafter, the DMF suspension described above was added to the mixed acid anhydride. The reaction mixture was reacted at −10° C. for 30 minutes and at 0° C. for 30 minutes. After DMF was distilled off under reduced pressure, ethyl acetate was added to the residue. The mixture was washed, in sequence, with 5% hydrochloric acid aqueous solution, saturated sodium chloride aqueous solution, 10% sodium hydrogencarbonate aqueous solution and saturated sodium chloride aqueous solution. After drying over MgSO$_4$, the reaction mixture was concentrated to give 1.30 g (30%) of the title compound as an oil.

TLC=Rf$_5$=0.17–0.22.
$[\alpha]_D^{20}$= −39° (C=0.25, DMF).

Elemental analysis as C$_{40}$H$_{47}$N$_7$O$_8$.H$_2$O: Calcd.: C 62.24%, H 6.40%, N 12.70%; Found: C 62.22%, H 6.21%, N 12.62%.

c)
N-α-Benzyloxycarbonyl-N-ε-benzoyl-D-lysyl-L-prolyl-N-G-benzyloxycarbonyl-L-arginine-δ-lactam
(synthesis by another route)

N-α-Benzyloxycarbonyl-D-lysyl-L-prolyl-N-G-benzyloxycarbonyl-L-arginine-δ-lactam (1.08 g, 1.5 mmol), chloroform (50 ml), 30% (w/w) potassium carbonate aqueous solution (3.6 ml) and benzoyl chloride (0.21 ml, 1.8 mmol) were treated in a manner similar to Example 3 d) to give 0.70 g (62%) of the title compound as an oil.

This sample quite coincided with the compound obtained by the procedures of Example 5 b) in behaviors of TLC and IR.

d)
N-α-Benzyloxycarbonyl-N-ε-benzoyl-D-lysyl-L-prolyl-N-G-benzyloxycarbonyl-L-argininal A solution of N-α-benzyloxycarbonyl-N-ε-benzoyl-D-lysyl-L-prolyl-N-G-benzyloxycarbonyl-L-arginine-δlactum (0.81 g, 1.07 mmol) in dry THF (6 ml) and a 0.4 M LiAlH$_4$ solution in dry THF (2.7 ml) were treated in a manner similar to Example 1 c) to give 0.51 g (63%) of the title compound as an oil.

TLC=Rf$_3$=0.44–0.51.

[α]$_D^{20}$= −5° (C=0.5, DMF).

Elemental analysis as C$_{40}$H$_{50}$N$_7$O$_8$.4/5H$_2$O: Calcd.: C 62.28%, H 6.74%, N 12.71%; Found: C 62.39%, H 6.72%, N 12.40%.

e) N-ε-Benzoyl-D-lysyl-L-prolyl-L-argininal sulfate

N-α-Benzyloxycarbonyl-N-ε-benzoyl-D-lysyl-L-prolyl-N-G-benzyloxycarbonyl-L-argininal (0.77 g, 1.02 mmol), 1 N sulfuric acid (1.94 ml, 1.94 mmol), 85% methanol (200 ml) and palladium black (1.0 g) were treated in a manner similar to Example 1 d) to give 0.38 g (64%) of the title compound.

TLC=Rf$_4$=0.28–0.52 mp: 162°–170° C.

[α]$_D^{20}$= −18° (C=0.5, DMF).

Elemental analysis as C$_{24}$H$_{39}$N$_7$O$_8$S.8/5H$_2$O: Calcd.: C 46.90%, H 6.92%, N 15.95%; Found: C 47.12%, H 6.80%, N 15.64%.

EXAMPLE 7

Synthesis of N-ε-(p-toluoyl)-D-lysyl-L-prolyl-L-argininal sulfate a)

N-α-Benzyloxycarbonyl-N-ε(p-toluoyl)-D-lysyl-L-prolyl-N-G-benzyloxycarbonyl-L-arginine-δ-lactam p-Toluoyl chloride (0.36 ml, 2.75 mmol) was used instead of 2-naphthalenesulfonyl chloride and treated in a manner similar to Example 3 d) to give 0.90 g (47%) of the title compound as an oil.

TLC=Rf$_4$=0.37–0.44.

[α]$_D^{24}$= −51° (C=0.25, DMF).

b)

N-α-Benzyloxycarbonyl-N-ε-(p-toluoyl)-D-lysyl-L-prolyl-N-G-benzyloxycarbonyl-L-argininal A solution of N-α-benzyloxycarbonyl-N-ε-(p-toluoyl)-D-lysyl-L-prolyl-N-G-benzyloxycarbonyl-L-arginine-δ-lactam (0.82 g, 1.06 mmol) in dry THF (6 ml) and a 0.4 M LiAlH$_4$ solution in dry THF (2.65 ml, 1.06 mmol) were treated in a manner similar to Example 1 c) to give 0.53 g (65%) of the title compound as an oil.

TLC=Rf$_5$ =0.16–0.26.

[α]$_D^{20}$= −7° (C=0.15, DMF).

Elemental analysis as C$_{40}$H$_{49}$N$_7$O$_8$.1/2H$_2$O: Calcd.: C 62.81%, H 6.59%, N 12.81%; Found: C 63.00%, H 6.75%, N 12.42%.

c) N-ε-(p-Toluoyl)-D-lysyl-L-prolyl-L-argininal sulfate

N-α-Benzyloxycarbonyl-N-ε-(p-toluoyl)-D-lysyl-L-prolyl-N-G-benzyloxycarbonyl-L-argininal (0.47 g, 0.61 mmol), 1 N sulfuric acid (1.10 ml), 85% methanol (150 ml) and palladium black (1.0 g) were treated in a manner similar to Example 1 d) to give 0.35 g (96%) of the title compound as crystals.

TLC=Rf$_4$=0.45–0.60 mp: 155° C. (dec.).

[α]$_D^{20}$= −18° (C=0.15, DMF).

Elemental analysis as C$_{25}$H$_{41}$N$_7$O$_8$S.3/2H$_2$O: Calcd.: C 47.91%, H 7.08%, N 15.64%; Found: C 47.62%, H 7.09%, N 15.43%.

EXAMPLE 8

Synthesis of N-ε-(2-naphthoyl)-D-lysyl-L-prolyl-L-argininal sulfate a)

N-α-Benzyloxycarbonyl-N-ε-(2-naphthoyl)-D-lysyl-L-prolyl-N-G-benzyloxycarbonyl-L-arginine-δ-lactam 2-Naphthoyl chloride (0.52 ml, 2.75 mmol) was used instead of 2-naphthalenesulfonyl chloride and treated in a manner similar to Example 3 d) to give 1.13 g (56%) of the title compound as an oil.

TLC=Rf$_5$=0.38–0.44.

b)

N-α-Benzyloxycarbonyl-N-ε-(2-naphthoyl)-D-lysyl-L-prolyl-N-G-benzyloxycarbonyl-L-argininal A solution of N-o-benzyloxycarbonyl-N-ε-(2-naphthoyl)-D-lysyl-L-prolyl-N-G-benzyloxycarbonyl-L-arginine-δ-lactam (1.04 g, 1.29 mmol) in dry THF (6 ml) and a 0.4 M LiAlH$_4$ solution in dry THF (3.3 ml, 1.29 mmol) were used and treated in a manner similar to Example 1 c) to give 0.58 g (56%) of the title compound as an oil.

TLC=Rf$_5$=0.18–0.26.

[α]$_D^{20}$= −13° (C=0.15, DMF).

Elemental analysis as C$_{44}$H$_{51}$N$_7$O$_8$.2H$_2$O: Calcd.: C 62.76%, H 6.58%, N 11.64%; Found: C 62.67%, H 6.18%, N 11.36%.

c) N-ε-(2-Naphthoyl)-D-lysyl-L-prolyl-L-argininal sulfate

N-α-Benzyloxycarbonyl-N-ε-(2-naphthoyl)-D-lysyl-L-prolyl-N-G-benzyloxycarbonyl L-argininal (0.51 g, 0.63 mmol), 1 N sulfuric acid (1.12 ml), 85% methanol and palladium black (1.0 g) were treated in a manner similar to EXAMPLE 1 d) to give 0.34 g (85%) of the title compound as crystals.

TLC=Rf$_4$=0.50–0.62; mp: 135° C. (dec.).

[α]$_D^{20}$ = −16° (C=0.5, DMF),

Elemental analysis as C$_{28}$H$_{41}$N$_7$O$_8$S.3/2H$_2$O: Calcd: C 50.74%, H 6.54%, N 14.79%; Found: C 50.52%, H 6.67%, N 15.00%.

EXAMPLE 9

Synthesis of N-ε-phenylacetyl-D-lysyl-L-prolyl-L-argininal sulfate a)

N-α-Benzyloxycarbonyl-N-ε-phenylacetyl-D-lysyl-L-prolyl-N-G-benzyloxycarbonyl-L-arginine-δ-lactam N-α-Benzyloxycarbonyl-D-lysyl-L-prolyl-N-G-benzyloxycarbonyl-L-arginine-δ-lactam hydrochloride (1.08 g, 1.5 mmol), chloroform (50 ml), 30% (w/w) potassium carbonate aqueous solution (3.6 ml) and phenylacetyl chloride (0.22 ml, 1.65 mmol) were treated in a manner similar to EXAMPLE 3 d) to give 0.60 g (52%) of the title compound.

TLC=Rf$_5$=0.31–0.46.

[α]$_D^{24}$= −49° (C=0.25, DMF).

Elemental analysis as C$_{41}$H$_{49}$N$_7$O$_8$.9/5H$_2$O: Calcd.: C 61.53%, H 6.62%, N 12.25%; Found: C 61.79%, H 6.83%, N 11.85%.

b) N-α-Benzyloxycarbonyl-N-ε-phenylacetyl-D-lysyl-L-prolyl-N-G-benzyloxycarbonyl-L-argininal A solution of N-α-benzyloxycarbonyl-N-ε-phenylacetyl-D-lysyl-L-prolyl-N-G-benzyloxycarbonyl-L-arginine-δ-lactam (0.54 g, 0.70 mmol) in dry THF (6 ml) and a 0.4 M LiAlH$_4$ solution in dry THF (1.75 ml) were used and treated in a manner similar to Example 1 c) to give 0.32 g (59%) of the title compound as an oil.

TLC=Rf$_5$=0.16-0.26.
$[\alpha]_D^{20}$= -13° (C=0.15, DMF).
Elemental analysis as C$_{41}$H$_{51}$N$_7$O$_8$.1/2H$_2$O: Calcd.: C 63.22%, H 6.73%, N 12.59%; Found: C 63.09%, H 6.74%, N 12.46%.

c) N-ε-Phenylacetyl-D-lysyl-L-prolyl-L-argininal sulfate

N-α-Benzyloxycarbonyl-N-ε-phenylacetyl-D-lysyl-L-prolyl-N-G-benzyloxycarbonyl-L-argininal (0.24 g, 0.31 mmol), 1 N sulfuric acid (0.56 ml), 85% methanol (150 ml) and palladium black (1 g) were treated in a manner similar to EXAMPLE 1 d) to give 0.14 g (75%) of the title compound as crystals.

TLC=Rf$_4$=0.35-0.62 mp: 140° C (dec.).
$[\alpha]_D^{20}$= -43° (C=0.15, H$_2$O:
Elemental analysis as C$_{25}$H$_{41}$N$_7$O$_8$S.3/2H$_2$O: Calcd.: C 47.91%, H 7.08%, N 15.64%; Found: C 47.85%, H 7.10%, N 15.61%.

EXAMPLE 10

Synthesis of N-ε-acetyl-D-lysyl-L-prolyl-L-argininal sulfate a) N-α-Benzyloxycarbonyl-N-ε-acetyl-D-lysyl-L-prolyl-N-G-benzyloxycarbonyl-L-arginine-δ-lactam Acetyl chloride (0.20 ml, 2.75 mmol) was used instead of 2-naphthalenesulfonyl chloride and treated in a manner similar to Example 3 d) to give 1.09 g (63%) of the title compound.
TLC=Rf$_5$=0.23-0.28.

b) N-α-Benzyloxycarbonyl-N-ε-acetyl-D-lysyl-L-prolyl-N-G-benzyloxycarbonyl-L-argininal A solution of N-α-benzyloxycarbonyl-N-ε-acetyl-D-lysyl-L-prolyl-N-G-benzyloxycarbonyl-L-arginine-δ-lactam (1.09 g, 1.58 mmol) in dry THF (5 ml) and 0.4 M LiAlH$_4$ solution in dry THF (3.95 ml, 1.58 mmol) were used and treated in a manner similar to Example 1 c) to give 0.61 g (55%) of the title compound.
TLC=Rf$_1$=0.38-0.43.
$[\alpha]_D^{20}$= -18° (C=0.3, DMF).
Elemental analysis as C$_{35}$H$_{47}$N$_7$O$_8$.3/2H$_2$O; Calcd.: C 58.32%, H 6.99%, N 13.60%; Found: C 58.23%, H 6.70%, N 13.44%.

c) N-ε-Acetyl-D-lysyl-L-prolyl-L-argininal sulfate

N-α-Benzyloxycarbonyl-N-ε-acetyl-D-lysyl-L-prolyl-N-G-benzyloxycarbonyl-L-argininal (0.51 g, 0.74 mmol), 1 N sulfuric acid (1.33 ml), 85% methanol (150 ml) and palladium black (1 g) were treated in a manner similar to Example 1 d) to give 0.35 g (90%) of the title compound.
TLC=Rf$_6$=0.27-0.48; mp: 140° C. (dec.).
$[\alpha]_D^{20}$= -58° (C=0.5, H$_2$O).
Elemental analysis as C$_{19}$H$_{37}$N$_7$O$_8$S.5/2H$_2$O: Calcd.: C 40.13%, H 7.44%, N 17.24%; Found: C 40.63%, H 7.46%, N 16.73%.

EXAMPLE 11

Synthesis of N-ε-propionyl-D-lysyl-L-prolyl-L-argininal sulfate a) N-α-Benzyloxycarbonyl-N-ε-propionyl-D-lysyl-L-prolyl-N-G-benzyloxycarbonyl-L-arginine-δ-lactam Triethylamine (0.70 ml, 5.0 mmol) was added to a solution of N-α-benzyloxycarbonyl-D-lysyl-L-prolyl-N-G-benzyloxycarbonyl-L-arginine-δ-lactam dihydrochloride (1.81 g, 2.50 mmol) in DMF (3.75 ml) at -10° C. The resulting suspension was added to the mixed acid anhydride prepared below.

After propionic acid (0.19 ml, 2.50 mmol) was dissolved in DMF (3 ml), the solution was cooled to -15° C. Then, N-methylmorpholine (0.27 ml, 2.50 mmol) and isobutyl chloroformate (0.36 ml, 2.50 mmol) were added, in sequence, to the solution. After completion of the addition, stirring was continued for 10 minutes. Thereafter, the DMF suspension described above was added to the resulting mixed acid anhydride The reaction mixture was reacted at -10° C. for an hour and at 0° C. for an hour. After DMF was distilled off under reduced pressure, chloroform (30 ml) was added to dissolve the residue. The mixture was washed, in sequence, with water, 5% hydrochloric acid aqueous solution, water, 10% NaHCO$_3$ aqueous solution and water. After dehydrating with MgSO$_4$, the solution was concentrated to give 0.86 g (49%) of the title compound as an oil.
TLC=Rf$_5$=0.57-0.63.

b) N-α-Benzyloxycarbonyl-N-ε-propionyl-D-lysyl-L-prolyl-N-G-benzyloxycarbonyl-L-argininal A solution of N-α-benzyloxycarbonyl-N-ε-propionyl-D-lysyl-L-prolyl-N-G-benzyloxycarbonyl-L-arginine-δ-lactam (0.86 g, 1.22 mmol) in dry THF (4 ml) and a 0.4 M LiAlH$_4$ solution in dry THF (3.05 ml, 1.22 mmol) were treated in a manner similar to EXAMPLE 1 c) to give 0.52 g (61%) of the title compound as an oil.
TLC=Rf$_1$=0.37-0.43.
$[\alpha]_D^{20}$= -23° (C=0.2, DMF).
Elemental analysis as C$_{36}$H$_{49}$N$_7$O$_8$.5/3H$_2$O: Calcd.: C 58.60%, H 7.15%, N 13.28%; Found: C 58.71%, H 6.74%, N 13.02%.

c) N-ε-Propionyl-D-lysyl-L-prolyl-L-argininal sulfate

N-α-Benzyloxycarbonyl-N-ε-propionyl-D-lysyl-L-prolyl-N-G-benzyloxycarbonyl-L-argininal (0.42 g, 0.59 mmol), 1 N sulfuric acid (1.07 ml), 85% methanol (150 ml) and palladium black (1.0 g) were treated in a manner similar to Example 1 d) to give 0.31 g (97%) of the title compound as crystals.
TLC=Rf$_6$=0.40-0.61; mp: 135° C. (dec.).
$[\alpha]_D^{20}$= -32° (C=0.5, DMF),
Elemental analysis as C$_{20}$H$_{39}$N$_7$O$_8$S.7/4H$_2$O: Calcd.: C 42.20%, H 7.53%, N 17.22%; Found: C 42.53%, H 7.77%, N 16.53%,

EXAMPLE 12

Synthesis of
N-ε-[trans-4-(aminomethyl)-cyclohexanecarbonyl]-D-lysylL-argininal 3/2 sulfate a)

N-α-Benzyloxycarbonyl-N-ε-[N-benzyloxycarbonyl-trans-4-(aminomethyl)cyclohexaneca-rbonyl]-D-lysylL-prolyl-N-G-benzyloxycarbonyl-L-arginine-δ-lactam After N-α-benzyloxycarbonyl-D-lysyl-L-prolyl-N-G-benzyloxycarbonyl-L-arginine-δ-lactam hydrochloride (1.0 g, 1.38 mmol) was dissolved in DMF (4 ml), the solution was cooled to −10° C. and triethylamine (0.39 ml, 2.76 mmol) was added to the solution. The resulting suspension was added to the mixed acid anhydride prepared below.

After N-benzyloxycarbonyl-trans-4-(aminomethyl)-cyclohexanecarboxylic acid (0.40 g, 1.38 mmol) was dissolved in DMF (3.3 ml), the solution was cooled to −15° C. Then, N-methylmorpholine (0.15 ml, 1.38 mmol) and isobutyl chloroformate (0.18 ml, 1.38 mmol) were added, in sequence, to the solution at the same temperature. After completion of the addition, stirring was continued for 10 minutes. Thereafter, the DMF suspension described above was added to the resulting mixed acid anhydride. The reaction mixture was reacted at −10° C. for an hour and at 0° C. for an hour. After DMF was distilled off with an evaporator, chloroform (15 ml) was added to the residue. The mixture was washed, in sequence, with water, 5% hydrochloric acid aqueous solution, water, 10% NaHCO$_3$ aqueous solution and water. After drying over MgSO$_4$, the solution was concentrated. The residue (1.19 g) was subjected to silica gel (119 g) column chromatography. Elution with chloroform-methanol gave 0.47 g (38%) of the title compound as an oil.

TLC=Rf$_5$=0.33–0.40.

b)

N-α-Benzyloxycarbonyl-N-ε-[N-benzyloxycarbonyl-trans-4-(aminomethyl)cyclohexanecarbonyl]-D-lysyl-L-prolyl-N-G-benzyloxycarbonyl-L-argininal A solution of N-α-benzyloxycarbonyl-N-ε-[N-benzyloxycarbonyl-trans-4-(aminomethyl)cyclohexanecarbonyl]-D-lysyl-L-prolyl-N-G-benzyloxycarbonyl-L-arginine-δ -lactam (0.97 g, 1.05 mmol) in dry THF (3.2 ml) and a 0.4 M LiAlH$_4$ solution in dry THF (2.6 ml, 1.05 mmol) were used and treated in a manner similar to Example 1 c) to give 0.51 g (53%) of the title compound as an oil.

TLC=Rf$_1$=0.59–0.63.

$[\alpha]_D^{20}$=−23° (C=0.1, DMF).

Elemental analysis as C$_{49}$H$_{64}$N$_8$O$_{10}$.3/2H$_2$O; Calcd.: C 61.81%, H 7.09%, N 11.76%; Found: C 61.91%, H 6.99%, N 11.56%.

c)

N-ε-[Trans-4-(aminomethyl)cyclohexanecarbonyl]-D-lysyl-L-prolyl-L-argininal 3/2 sulfate N-α-Benzyloxycarbonyl-N-ε-[N-benzyloxycarbonyl-trans-4-(aminomethyl)cyclohexanecarbonyl]-D-lysyl-L-prolyl-N G-benzyloxycarbonyl-L-argininal (0.41 g, 0.44 mmol), 85% methanol (150 ml), 1 N sulfuric acid (1.2 ml) and palladium black (1.0 g) were treated in a manner similar to Example 1 d) to give 0.23 g (100%) of the title compound as crystals.

TLC=Rf$_6$=0.04–0.22; mp: 70° C. (dec.).

$[\alpha]_D^{20}$=−43° (C=0.5, H$_2$O).

Elemental analysis as C$_{25}$H$_{49}$N$_8$O$_{10}$S$_{1.5}$.3/2H$_2$O: Calcd.: C 43.09%, H 7.52%, N 16.08%; Found: C 43.18%, H 7.93%, N 16.00%.

EXAMPLE b 13

Synthesis of
N-α-methoxycarbonyl-N-ε-(p-tosyl)-D-lysyl-L-prolyl-L-argininal hydrochloride a)

N-α-Methoxycarbonyl-N-ε-(p-tosyl)-D-lysyl-L-proline

N-ε-(p-Tosyl)-D-lysine (18.0 g, 60 mmol) was dissolved in a solvent mixture of methanol (150 ml) and 2 N sodium hydroxide aqueous solution (600 ml). The solution was cooled to 0° to 5° C. and stirred. While maintaining the same temperature, methoxycarbonyl chloride (7.73 ml, 100 mmol) was dropwise added to the solution over 30 minutes. In this case, the pH was maintained at 8 or more, if necessary, by appropriately supplementing 4 N sodium hydroxide aqueous solution. While maintaining the pH at 8, the reaction mixture was stirred at 0° C. for 2 hours and at room temperature for an hour. After completion of the reaction, the pH of the reaction mixture was adjusted to 2 with 5 N hydrochloric acid aqueous solution. After extracting with ethyl acetate, the extract was washed with chilled 5% hydrochloric acid and then with saturated sodium chloride aqueous solution. After drying over MgSO$_4$, the extract was concentrated to give 22.1 g (103%) of N-α-methoxycarbonyl-N-ε-(p-tosyl)-D-lysine as an oil.

TLC=Rf$_1$=0.33–0.44.

A suspension of N-α-methoxycarbonyl-N-ε-(p-tosyl)-D-lysine (7.4 g, 20.6 mmol), 2-mercapto-4,6-dimethylpyrimidine (3.5 g, 24.8 mmol) and ethyl acetate (40 ml) was cooled to 0°–5° C. DCC (4.3 g, 20.6 mmol) was added to the suspension. The reaction mixture was stirred overnight at room temperature. The precipitated crystals were filtered and the filtrate was washed with 10% NaHCO$_3$ aqueous solution and then with saturated sodium chloride aqueous solution. After drying over MgSO$_4$, the filtrate was concentrated to give 9.9 g (100%) of N-α-methoxycarbonyl-N-ε-(p-tosyl)-D-lysine-4,6-dimethylpyrimidin-2-ylthiol ester as an oil.

This activated ester (20.6 mmol) was dissolved in THF (20 ml). The activated ester solution in THF was added to a suspension of L-proline (2.6 g, 22.7 mmol) and triethylamine (5.1 ml, 36 mmol) in water (28 ml) at room temperature followed by stirring overnight at room temperature. The reaction solution was concentrated to a volume of ⅓. After water (31 ml) was added to the concentrate, the mixture was washed with ethyl acetate. A pH of the aqueous layer was adjusted to 2 with chilled 5 N hydrochloric acid. After extracting with ethyl acetate, the extract was washed with chilled 5% hydrochloric acid and with saturated sodium chloride aqueous solution. After drying over MgSO$_4$, the extract was concentrated to give 6.8 g (73%) of N-α-methoxy-carbonyl-N-ε-(p-tosyl)-D-lysyl-L-proline as an oil.

TLC=Rf$_1$=0.37–0.48.

$[\alpha]_D^{20}$=−20° (C=0.5, DMF).

Elemental analysis as C$_{20}$H$_{28}$N$_3$O$_7$S: Calcd.: C 52.73%, H 6.42%, N 9.22%; Found: C 52.43%, H 6.73%, N 8.76%.

b)

N-α-Methoxycarbonyl-N-ε-(p-tosyl)-D-lysyl-L-prolyl-N-G-benzyloxycarbonyl-L-arginine-δ-lactam To a solution of N-G-benzyloxycarbonyl-L-arginine-6-lactam (5.3 g, 14.3 mmol) in DMF (16 ml) was added triethylamine (4.0 ml, 28.6 mmol) at −10° C. The resulting suspension was added to the mixed acid anhydride prepared below.

After N-α-methoxycarbonyl-N-ε-(p-tosyl)-D-lysyl-L-proline (6.5 g, 14.3 mmol) was dissolved in DMF (21 ml), the solution was cooled to −15° C. The solution was cooled to −15° C. and then N-methylmorpholine (1.57 ml, 14.3 mmol) and isobutyl chloroformate (1.85 ml, 14.3 mmol) were added, in sequence, to the solution at the same temperature. After completion of the addition, stirring was continued for 10 minutes. Thereafter, the DMF suspension described above was added to the mixed acid anhydride obtained. The reaction mixture was reacted at −10° C. for an hour and at 0° C. for an hour. After DMF was distilled off, ethyl acetate (600 ml) was added to the residue. The mixture was washed, in sequence, with chilled 1% hydrochloric acid aqueous solution, saturated sodium chloride aqueous solution, 10% $NaHCO_3$ aqueous solution and saturated sodium chloride aqueous solution. After drying over $MgSO_4$, the solution was concentrated to give 5.3 g (51%) of the title compound as an oil.

TLC=$Rf_2$ =0.33–0.48.

c)

N-α-Methoxycarbonyl-N-ε-(p-tosyl)-D-lysyl-L-prolyl-N-G-benzyloxycarbonyl-L-argininal A solution of N-α-methoxycarbonyl-N-ε-(p-tosyl)-D-lysyl-L-prolyl-N-G-benzyloxycarbonyl-L-arginine-δ-lactam (5.2 g, 7.2 mmol) in dry THF (25 ml) and a dry THF solution (18 ml, 7.2 mmol) containing 0.4 M $LiAlH_4$ were used and treated in a manner similar to Example 1 c) to give 3.2 g (61%) of the title compound as an oil.

TLC=$Rf_5$=0.21–0.38.

Elemental analysis as $C_{34}H_{47}N_7O_9S.5/2H_2O$: Calcd.: C 52.70%, H 6.76%, N 12.65%; Found: C 52.50%, H 6.21%, N 12.32%.

d)

N-α-Methoxycarbonyl-N-ε-(p-tosyl)-D-lysyl-L-prolyl-L-argininal hydrochloride

N-α-Methoxycarbonyl-N-ε-(p-tosyl)-D-lysyl-L-prolyl-N-G-benzyloxycarbonyl-L-argininal (3.1 g, 4.2 mmol), 5% hydrogen chloride-methanol (3.06 ml, 4.2 mmol), 85% methanol (150 ml) and palladium black (1.0 g) were treated in a manner similar to Example 1 d) to give 2.6 g (99%) of the title compound as crystals.

TLC=$Rf_7$=0.46–0.55 mp; 105°–140° C. (dec.).

$[\alpha]_D^{20}$= −23° (C=0.5, DMF),

Elemental analysis as $C_{26}H_{44}N_7O_8SCl.3/2H_2O$; Calcd.: C 47.37%, H 6.88%, N 14.87%; Found: C 47.75%, H 6.91%, N 14.29%.

EXAMPLE 14

Synthesis of
N-α-isobutoxycarbonyl-N-ε-(p-tosyl)-D-lysyl-L-prolyl-L-argininal hydrochloride a)

N-α-Isobutoxycarbonyl-N-ε-(p-tosyl)-D-lysyl-L-proline

Following the procedures for synthesis of N-α-methoxycarbonyl-N-ε-(p-tosyl)-D-lysin in Example 13 a) using isobutoxycarbonyl chloride (13.0 g, 0.1 mmol) in place of methoxycarbonyl chloride, 25.4 g (100%) of N-α-isobutoxycarbonyl-N-ε-(p-tosyl)-D-lysin was obtained as an oil.

TLC=Rf=0.38–0.43.

Following the procedures for synthesis of N-α-methoxycarbonyl-N-ε-(p-tosyl)-D-lysin-4,6-dimethylpyrimidin-2-ylthiol ester in Example 13 a), N-α-isobutoxycarbonyl-N-ε-(p-tosyl)-D-lysin-4,6-dimethylpyrimidin-2-ylthiol ester was quantitatively obtained as an oil, using N-α-isobutoxycarbonyl-N-ε-(p-tosyl)-D-lysin (6.0 g, 15 mmol), 2-mercapto-4,6-dimetylpyrimidine (2.5 g, 18 mmol), ethyl acetate (50 ml) and DCC (3.1 g, 15 mmol).

This activated ester (15 mmol), THF (21 ml), L-proline (1.9 g, 16 mmol), triethylamine (3.8 ml, 27 mmol) and water (21 ml) were treated following the procedures for synthesis of N-α-methoycarbonyl-N-ε-(p-tosyl)-D-lysyl-L-proline in Example 13 a). Thus, 3.7 g (50%) of N-α-isobutoxycarbonyl-N-ε-(p-tosyl)-D-lysylL-proline was obtained as an oil.

TLC=$Rf_1$=0.38–0.49.

$[\alpha]_D^{24}$= −14° (C=0.25, DMF.

b)

N-α-Isobutoxycarbonyl-N-ε-(p-tosyl)-D-lysyl-Lprolyl-N-G-benzyloxycarbonyl-L-arginine-δ-lactam Using N-α-isobutoxycarbonyl-N-ε-(p-tosyl)D-lysyl-L-proline (3.5 g, 7.0 mmol) in place of N-α-methoxycarbonyl-N-ε-(p-tosyl) D-lysyl-L-proline, reactants were treated in a manner similar to Example 13 b) in a proportional molar ratio to give 2.9 g (54%) of the title compound as an oil.

TLC=$Rf_2$=0.34–0.42.

c)

N-α-Isobutoxycarbonyl-N-ε-(p-tosyl)-D-lysyl-L-prolyl-N-G-benzyloxycar,bonyl-L-argininal A solution of N-α-isobutoxycarbonyl-N-ε-(p-tosyl)-D-lysyl-L-prolyl-N-G-benzyloxycarbonyl-L-arginine-6-lactam (2.7 g, 3.5 mmol) in dry THF (15 ml) and a 0.4 M $LiAlH_4$ solution in dry THF (8.8 ml, 3.5 mmol) were used and treated in a manner similar to Example 1 c) to give 1.8 g (67%) of the title compound as an oil.

TLC=$Rf_5$=0.32–0.46.

Elemental analysis as $C_{37}H_{53}N_7O_9S.3/2H_2O$: Calcd: C 55.62%, H 7.07%, N 12.27%;

Found: C 55.71%, H 6.92%, N 12.27%;

d)

N-α-Isobutoxycarbonyl-N-ε-(p-tosyl)-D-lysyl-L-prolyl-L-argininal hydrochloride

N-α-Isobutoxycarbonyl-N-ε-(p-tosyl)-D-lysyl-L-prolyl-N-G-benzyloxycarbonyl-L-argininal (1.7 g, 2.2 mmol), 5% hydrogen chloride-methanol (1.16 ml, 2.2 mmol), 85% methanol (150 ml) and palladium black (1.0 g) were treated in a manner similar to Example 1 d) to give 1.41 g (95%) of the title compound as crystals.
TLC=$Rf_7$=0.32-0.42; mp: 135° C. (dec.).
$[\alpha]_D^{20}$= −23° (C=0.3, DMF).
Elemental analysis as $C_{29}H_{48}N_7O_8SCl.3/4H_2O$: Calcd.: C 49.35%, H 7.35%, N 13.89%; Found: C 49.71%, H 7.27%, N 13.44%.

Example 15

Synthesis of
N-α-isobutoxycarbonyl-N-ε-(p-tosyl)-D-lysyl-L-prolyl-L-argininal ½ sulfate N-α-Isobutoxycarbonyl-N-ε-(p tosyl)-D-lysyl-L-prolyl-N-G-benzyloxycarbonyl-L-argininal (0.45 g, 0.58 mmol), 1 N sulfuric acid aqueous solution (0.55 ml), 85% methanol (150 ml) and palladium black (0.5 g) were used and treated in a manner similar to Example 1 d) to give 1 0.34 g (84%) of the title compound.
TLC=$Rf_7$=0.18-0.27 mp: 62°-63° C.
$[\alpha]_D$= −24° (C=0.25, DMF).
Elemental analysis as $C_{29}H_{48}N_7O_9S_{1.5}.2H_2O$: Calcd.: C 48.18%, H 7.25%, N 13.56%; Found: C 48.26%, H 7.17%, N 13.20%.

EXAMPLE 16

Synthesis of
N-α-N-ε-di(p-tosyl)-D-lysyl-L-prolyl-L-argininal hydrochloride a)
N-α-(t-butoxycarbonyl)-N-ε-(p-tosyl)-D-lysyl-L-proline Using N-α-(t-butoxycarbonyl)-N-ε-(p-tosyl)-D-lysine (72.0 g, 180 mmol) in place of N-α-benzyloxy-carbonyl-N-ε-(p-tosyl)-D-lysine, reactants were treated in a manner similar to Example 1 a) in a proportional molar ratio to give 94 g (100%) of N-α-(t-butoxy-carbonyl)-N-ε-(p-tosyl)-D-lysine-4,6-dimethylpyrimidin-2-ylthiol ester as an oil.

Using this activated ester (180 mmol), reactants were treated in a manner similar to the coupling reaction in Example 1 a) in a proportional molar ratio to give 70.0 g (78%) of the title compound as an oil.
TLC=$Rf_1$=0.44-0.56.
$[\alpha]_D^{20}$= −20° (C=0.5, DMF).

b)
N-α-(t-Butoxycarbonyl)-N-ε-(p-tosyl)-D-lysyl-L-prolyl N-G-benzyloxycarbonyl-L-arginine-δ-lactam Using N-α-(t-butoxycarbonyl)-N-ε-(p-tosyl)-D-lysyl-L-proline (69.5 g, 140 mmol) in place of N-α-methoxycarbonyl-N-ε-(p-tosyl)-D-lysyl-L-proline, reactants were treated in a manner similar to Example 13 b) in a proportional molar ratio to give 102.1 g (95%) of the title compound as an oil.
TLC=$Rf_2$=0.33−0.46.
$[\alpha]_D^{20}$= −39° (C=0.5, DMF).
Elemental analysis as $C_{37}H_{51}N_7O_9S.11/5H_2O$: Calcd.: C 54.89%, H 6.90%, N 12.11%; Found: C 54.68%, H 7.03%, N 11.97%.

c)
N-ε-(p-Tosyl)-D-lysyl-L-prolyl-N-G-benzyloxy-carbonyl-L-arginine-δ-lactam dihydrochloride After N-α-(t-butoxycarbonyl)-N-ε-(p-tosyl)-D-lysyl-L-prolyl-N-G-benzyloxycarbonyl-L-arginine-δ-lactam (97.1 g, 0.126 mmol) was dissolved in 2 N hydrogen chloride acetic acid solution (315 ml, 630 mmol), the solution was stirred at room temperature for 2 hours. After completion of the reaction, the reaction mixture was poured onto dry ether (5 l) and the precipitated crystals were taken by filtration to give 82.1 g (88%) of the title compound as an oil.
TLC=$Rf_8$=0.36-0.41; mp 110°-135° C. (dec.).
$[\alpha]_D^{20}$= −42° (C=0.41, DMF).
Elemental analysis as $C_{32}H_{45}N_7O_7SCl_2.5/2H_2O$: Calcd.: C 49.93%, H 6.29%, N 12.74%; Found: C 50.14%, H 6.33%, N 12.59%.

d)
N-α-N-ε-di(p-tosyl)-D-lysyl-L-prolyl-N-G-benzyloxycarbonyl-L-arginine-δ-lactam After N-ε-(p-tosyl)-D-lysyl-L-prolyl-N-G-benzyloxycarbonyl-L-arginine-δ-lactam (7.4 g, 10 mmol) was dissolved in DMF (20 ml), the solution was stirred under ice cooling. To the solution were added a 1.5 N N-ethylmorpholine solution in DMF (20 ml, 30 mmol) and then p-tosyl chloride (1.9 g, 10 mmol). After completion of the addition, the mixture was reacted for an hour under ice cooling. Ethyl acetate (600 ml) was added to the reaction mixture followed by washing, in sequence, with 0.1 N hydrochloric acid aqueous solution, saturated sodium chloride aqueous solution, 10% $NaHCO_3$ and saturated sodium chloride aqueous solution. After drying over $MgSO_4$, the mixture was concentrated to give 5.5 g (67%) of the title compound.
TLC=Rf=0.25-0.35.

e) N-α-N-68
-di(p-tosyl)-D-lysyl-L-prolyl-N-G-benzyl-oxycarbonyl-L-argininal

A solution of N-α-N-ε-di(p-tosyl)-D-lysyl-L-prolyl-N-G-benzyloxycarbonyl-L-arginine-δ-lactam (5.4 g, 6.6 mmol) in dry THF (20 ml) and a 0.4 M $LiAlH_4$ solution in dry THF (16.5 ml, 6.6 mmol) were treated in a manner similar to Example 1 c) to give 2.8 g (51%) of the title compound.
TLC=$Rf_5$=0.15-0.25 mp: 170°-180° C. (dec.).
Elemental analysis as $C_{39}H_{51}N_7O_9S_2.13/10H_2O$: Calcd.: C 55.15%, H 6.36%, N 11.54%; Found: C 55.36%, H 6.28%, N 11.19%.

f)
N-α-N-ε-di(p-tosyl)-D-lysyl-L-prolyl-N-G-benzyloxycarbonyl-L-argininal hydrochloride N-α-N-ε-di(p-tosyl)-D-lysyl-L-prolyl-N-G-benzyloxycarbonyl-L-argininal (2.6 g, 3.2 mmol), 1.37 N hydrogen chloride-methanol solution (2.34 ml, 3.2 mmol), 85%, methanol (150 ml) and palladium black (1 g) were used and treated in a manner similar to Example 1 d) to give 1.73 g (74%) of the title compound.
TLC=$Rf_7$ =0.64-0.74 mp: 130°-145° C. (dec.).
$[\alpha]_D^{20}$= −24° (C=0.5, DMF).
Elemental analysis as $C_{31}H_{46}N_7O_7SCl.2H_2O$: Calcd.: C 48.77%, H 6.59%, N 12.82%; Found: C 48.39%, H 6.44%, N 12.71%.

Example 17

Synthesis of
N-α-N-ε-di(p-tosyl)-D-lysyl-L-prolyl-L-argininal ½ sulfate

N-α-N-ε-di(p-tosyl)-D-lysyl-L-prolyl-N-G-benzyloxycarbonyl-L-argininal (0.16 g, 0.20 mmol), 1 N sulfuric acid (0.19 ml), 85% methanol (25 ml) and palladium black (1 g) were used and treated in a manner similar to Example 1 d) to give 0.14 g (100%) of the title compound.
TLC=Rf$_7$=0.16-0.26 mp: 141°-142° C.
[α]$_D^{20}$= -42° (C=0.03, DMF).
Elemental analysis as C$_{31}$H$_{26}$N$_7$O$_9$S$_{2.5}$.5/2H$_2$O: Calcd.: C 47.38%, H 6.54%, N 12.47%; Found: C 47.11%, H 6.20%, N 12.38%.

EXAMPLE 18

Synthesis of
N-α-mesitylenesulfonyl-N-ε-(p-tosyl)-D-lysyl-L-prolyl-L-argininal hydrochloride a)

N-α-Mesitylenesulfonyl-N-ε-(p-tosyl)-D-lysyl-L-prolyl-N-G-benzyloxycarbonyl-L-arginine-ε-lactam Mesitylenesulfonyl chloride (2.2 g, 10 mmol) was used instead of p-tosyl chloride and treated in a manner similar to Example 16 d) to give 5.1 g (60%) of the title compound as an oil.
TLC=Rf$_2$=0.25-0.38.

b)

N-α-Mesitylenesulfonyl-N-ε-(p-tosyl)-D-lysyl-L-prolyl-N-G-benzyloxycarbonyl-L-argininal A solution of N-α-mesitylenesulfonyl-N-ε-(p-tosyl)-D-lysyl-L-prolyl-N-G-benzyloxycarbonylL-arginine-δ-lactam (4.9 g, 5.75 mmol) in dry THF (20 ml) and a 0.4 M LiAlH$_4$ solution in dry THF (14.4 ml, 5.75 mmol) were treated in a manner similar to Example 1 c) to give 1.70 g (35%) of the title compound as an oil.
TLC=Rf$_5$=0.15-0.35.
Elemental analysis as C$_{41}$H$_{55}$N$_7$O$_9$S$_2$.H$_2$O: Calcd.: C 56.47%, H 6.59%, N 11.24%; Found: C 56.81%, H 6.43%, N 10.76%.

c)

N-α-Mesitylenesulfonyl-N-ε-(p-tosyl)-D-lysyl-L-prolyl-L-argininal hydrochloride

N-α-Mesitylenesulfonyl-N-ε-(p-tosyl)-D-lysyl-L-prolyl-N-G-benzyloxycarbonyl-L-argininal (1.26 g, 1.41 mmol), 1 N hydrochloric acid (1.41 ml), 85% methanol (150 ml) and palladium black (1 g) were used and treated in a manner similar to Example 1 d) to give 0.96 g (90%) of the title compound.
TLC=Rf$_7$=0.68-0.76 mp: 113°-140° C. (dec.).
[α]$_D^{20}$= -17° (C=0.5, DMF).
Elemental analysis as C$_{33}$H$_{52}$N$_7$O$_8$S$_2$Cl.3/2H$_2$O: Calcd.: C 50.49%, H 6.93%, N 12.26%; Found: C 50.49%, H 6.81%, N 12.51%.

Example 19

Synthesis of
N-α-(2-naphthalenesulfonyl)-N-ε-(p-tosyl)-D-lysyl-L-prolyl-L-argininal hydrochloride a)

N-α-(2-Naphthalenesulfonyl)-N-ε-(p-tosyl)-D-lysyl-L-prolyl-N-G-benzyloxycarbonyl-L-arginine-δ-lactam Using 2-naphthalenesulfonyl chloride (2.3 g, 10 mmol) in place of p-tosyl chloride, reactants were treated in a manner similar to Example 16 d) in a proportional molar ratio to give 5.0 g (58%) of the title compound as an oil.
TLC=Rf$_2$=0.26-0.38.

b)

N-α-(2-Naphthalenesulfonyl)-N-ε-(p-tosyl)-D-lysyl-L-prolyl-N-G-benzyloxycarbonyl-L-argininal A solution of N-α-(2-naphthalenesulfonyl)-N-ε-(p-tosyl)-D-lysyl-L-prolyl-N-G-benzyloxycarbonyl-L-arginine-δ-lactam (4.9 g, 5.7 mmol) in dry THF (20 ml) and a 0.4 M LiAlH$_4$ solution in dry THF (14.5 ml, 5.7 mmol) were treated in a manner similar to Example 1 c) to give 1.8 g (37%) of the title compound as an oil.
TLC=Rf$_5$=0.17-0.39.

c)

N-α-(2-Naphthalenesulfonyl)-N-ε-(p-tosyl)-D-lysyl-L-prolyl-L-argininal hydrochloride N-α-(2-Naphthalenesulfonyl)-N-ε-(p-tosyl)-D-lysyl-L-prolyl-N-G-benzyloxycarbonyl-L-argininal (1.66 g, 1.93 mmol), 1 N hydrochloric acid aqueous solution (1.93 mmol), 85% methanol (150 ml) and palladium black (1 g) were treated in a manner similar to Example 1 d) to give 1.04 g (70%) of the title compound.
TLC=Rf$_7$=0.68-0.77; mp: 115°-130 ° C. (dec.).
[α]$_D^{20}$= -33° (C=0.5, DMF).
Elemental analysis as C$_{34}$H$_{46}$N$_7$O$_7$S$_2$Cl.3/2H$_2$O: Calcd: C 51.60%, H 6.24%, N 12.39%; Found: C 51.62%, H 6.42%, N 12.19%.

Example 20

Synthesis of
N-α-(2-naphthalenesulfonyl)-N-ε-(p-tosyl)-D-lysyl-L-prolyl-L-argininal ½ sulfate N-α-(2-Naphthalenesulfonyl)-N-ε-(p-tosyl)-D-lysyl-L-prolyl-N-ε-(benzyloxycarbonyl)-L-argininal (0.65 g, 0.76 mmol), 1 N sulfuric acid aqueous solution (0.72 ml), 85% methanol (20 ml) and palladium black (1.0 g) were used and treated in a manner similar to Example 1 d) to give 0.46 g (78%) of the title compound.
TLC=Rf$_7$=0.20-0.27; mp: 126° C. (dec.).
[α]$_D^{20}$= -31° (C=0.5, DMF).
Elemental analysis as C$_{34}$H$_{46}$N$_7$O$_9$S$_{2.5}$.5/2H$_2$O: Calcd: C 49.68%, H 6.25%, N 11.93%; Found: C 49.64%, H 6.06%, N 11.75%.

Example 21

Synthesis of
N-α-(n-octanoyl)-N-ε-(p-tosyl)-D-lysyl-L-prolyl-L-argininal hydrochloride a)

N-α-(n-Octanoyl)-N-ε-(p-tosyl)-D-lysyl-L-prolyl-N-G-benzyloxycarbonyl-L-arginine-δ-lactam A suspension of n-octanoic acid (2.9 g, 20 mmol), 2-mercapto-4,6-dimethylpyrimidine (3.1 g, 22 mmol) and ethyl acetate (40 ml) was cooled to 0° to 5° C. DCC (4.1 g, 20 mmol) was added to the suspension in a crystalline state and the reaction mixture was stirred overnight at room temperature. The precipitated crystals were filtered out and the filtrate was washed with 10% NaHCO$_3$ aqueous solution and then with sodium chloride aqueous solution. After drying over MgSO$_4$, the filtrate was concentrated to give 5.6 g (100%) of n-octanoic acid-4,6-dimethylpyrimidin-2-ylthiol ester as an oil.
N-ε-(p-Tosyl)-D-lysyl-L-prolyl-N-G-benzyloxycarbonyl-L-arginine-δ-lactam hydrochloride (7.4 g, 10 mmol) was dissolved in DMF (20 ml) and the solution was ice-cooled. To the solution was added a 1.5 N N- ethylmorpholine solution in DMF (13.3 ml), 20 mmol). The resulting suspension was added to N-ε-(p-tosyl)-D-lysyl-L-prolyl-N-G-benzyloxycarbonylL-arginine-δ-lactam (10 mmol) and the mixture was stirred overnight at room temperature. After completion of the addition, ethyl acetate (600 ml) was added to the reaction mixture followed by washing, in sequence, with 1% hydrochloric acid aqueous solution, saturated chloride aqueous solution, 10% $NaHCO_3$ and saturated sodium chloride aqueous solution. After drying over $MgSO_4$, the mixture was concentrated to give 5.1 g (64%) of the title compound.

TLC=$Rf_2$=0.20-0.31.

b)
N-α-(n-Octanoyl)-N-ε-(p-tosyl)-D-lysyl-L-prolyl-N-G-benzyloxycarbonyl-L-argininal A solution of N-α-(n-octanoyl)-N-ε-(p-tosyl)-D-lysyl-L-prolyl-N-G-benzyloxycarbonyl-L-arginine-δ-lactam (5.0 g, 6.3 mmol) in dry THF (20 ml) and a 0.4 M $LiAlH_4$ solution in dry THF (15.8 ml, 6.3 mmol) solution were treated in a manner similar to Example 1 c) to give 2.7 g (54%) of the title compound as an oil.

Elemental analysis as $C_{40}H_{59}N_7O_8S.3/2H_2O$: Calcd: C 58.26%, H 7.58%, N 11.89%; Found: C 58.25%, H 7.36%, N 11.55%.

c)
N-α-(n-Octanoyl)-N-ε-(p-tosyl)-D-lysyl-L-prolyl-L-argininal hydrochloride

N-α-(n-Octanoyl)-N-ε-(p-tosyl)-D-lysyl-L-prolyl-N-G-benzyloxycarbonyl-L-argininal (2.6 g, 3.25 mmol), 1 N hydrochloric acid aqueous solution (3.25 ml), 85% methanol (150 ml) and palladium black (1 g) were treated in a manner similar to Example 1 d) to give 2.0 g (88%) of the title compound.

TLC=$Rf_7$=0.73-0.81; mp: 80°-110° C. (dec.).
$[\alpha]_D^{20}$= −21° (C=0.5, DMF).
Elemental analysis as $C_{32}H_{54}N_7O_6SCl.2H_2O$: Calcd: C 52.19%, H 7.94%, N 13.31%; Found: C 51.82%, H 7.82%, N 13.28%.

EXAMPLE 22

Next, representative test examples on some of the serine protease inhibitors are shown and specifically explained. The test results of the compounds of this invention are shown in Table 3 by referring to the numbering used in EXAMPLES hereinbefore. For comparison, structures of known protease inhibitors are shown in Table 1 and the test results are shown in Table 2.

As synthetic substrate used to examine the activity of the inhibitor for inhibiting substrate decomposition with the enzyme, there were used PS-994 (H-D-Lys(Tos)-Phe-Lys-CHA.2HCl, manufactured by Nitto Boseki Co., Ltd.) for plasmin, PS-915 (H-D-Phe-Pro-Arg-CHA.2HCl, manufactured by Nitto Boseki Co., Ltd.) for thrombin and trypsin, PS-2000 (Z-D-Lys(HCO)-Gly-Arg-CHA.HCl, manufactured by Nitto Boseki Co., Ltd.) for factor Xa, S-2302 (H-D-Pro-Phe-Arg-pNA, manufactured by Kabi Co.) for kallikrein, and MUK-34:

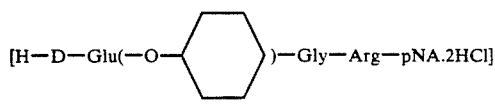
[H—D—Glu(—O—⟨ ⟩)—Gly—Arg—pNA.2HCl]

for urokinase.

As plasmin, thrombin, trypsin, factor Xa, kallikrein and urokinase, there were used 0.3 CU/ml of Sankyo Color Test $\alpha_2$-PI Assay Kit Standard, 1.2 NIH U/ml of Sankyo Color Test ATIII Assay Kit, 2 μg/ml of Code 3703 manufactured by Worsingstone Co., 0.25 U/ml of human factor Xa manufactured by Boehringer Mannheim, 0.12 U/ml of human plasma kallikrein manufactured by Kabi Co., and 1000 U/ml of Mochida Pharmaceutical Urokinase 60,000 (60,000 U/vial), respectively. In the case of CHA type substrate, a color-forming termination solution for Sankyo Color Test Kit was used. Enzyme reactions were carried out at 37° C.

Assay For Inhibitory Activity Against Plasmin

Each aqueous solution (0.1 ml) of the inhibitor having various concentrations was added to 0.4 ml of buffer (150 mM sodium chloride aqueous solution containing 100 mM Tris, pH 7.8) and the mixture was heated for 5 minutes. After 0.2 ml of the plasmin solution was added thereto, the mixture was reacted for 5 minutes. After 0.1 ml of PS-994 solution (10 mM) was added thereto, and the mixture was again reacted for 5 minutes. Then, 2.0 ml of the color-forming termination solution was added to the reaction mixture. Then the mixture was allowed to stand for 10 minutes and absorbance was measured at 700 nm. A concentration of the inhibitor in the reaction system showing ½ absorbance that of the case where no inhibitor was present was determined to be $IC_{50}$.

Assay For Inhibitory Activity Against Thrombin

Each aqueous solution (0.1 ml) of the inhibitor having various concentrations was added to 0.4 ml of buffer (150 mM sodium chloride aqueous solution containing 150 mM Tris, pH 8.5) and the mixture was heated for 5 minutes. Then, 0.2 ml of the thrombin solution was added thereto and the mixture was reacted for 5 minutes. After 0.1 ml of PS-915 solution (10 mM) was added thereto, the mixture was again reacted for 5 minutes. Then, 2 ml of the color-forming termination solution was added to the reaction mixture. Then the mixture was allowed to stand for 10 minutes and absorbance was measured at 700 nm. $IC_{50}$ was determined by the method described above.

Assay For Inhibitory Activity Against Trypsin

After 0.1 ml of an aqueous solution of the inhibitor was added to 0.5 ml of buffer (150 mM sodium chloride aqueous solution containing 150 mM Tris, pH 8.0) and the mixture was heated for 5 minutes, 0.1 ml of trypsin solution was added thereto. The mixture was reacted for 5 minutes. Furthermore, 0.1 ml of PS-915 solution (10 mM) was added thereto. The mixture was again reacted for 5 minutes. Then, 2 ml of the color-forming termination solution [containing 2.5 mg/ml of soybean trypsin inhibitor (manufactured by Sigma Co., No. T-9003)] was added to the reaction mixture. Then the mixture was allowed to stand for 10 minutes and absorbance was measured at 700 nm. $IC_{50}$ was determined by the method described above.

Assay For Inhibitory Activity Against Factor Xa

To 0.3 ml of buffer (150 mM sodium chloride aqueous solution containing 50 mM Tris, pH 8.5) was added 0.1 ml each of an aqueous solution of the inhibitor having various concentrations. The mixture was heated for 5 minutes. Then, 0.1 ml of factor Xa solution (150 mM solution chloride aqueous solution containing 50 mM Tris and 20 mM calcium chloride, pH 8.5) was added thereto, and the mixture was reacted for 5 minutes. Furthermore, 5% polyvinylpyrrolidone solution (0.1 ml) containing 10 mM PS-2000 was added thereto, and the mixture was again reacted for 5 minutes. Then, 2 ml of the color-forming termination solution was added to the reaction mixture. Then the mixture was allowed to stand for 10 minutes and absorbance was measured at 700 nm. $IC_{50}$ was determined by the method described above.

Assay For Inhibitory Activity Against Kallikrein

To 0.4 ml of buffer (150 mN sodium chloride aqueous solution containing 50 mM Tris, pH 8.0) was added 0.1 ml each of aqueous solutions of the inhibitor having various concentrations and the mixture was heated for 5 minutes. Then, 0.1 ml of kallikrein solution (containing 0.5% bovine serum albumin, No. A-8022 of Sigma Co.) was added thereto, and the mixture was reacted for 5 minutes. Furthermore, 10 mM S-2302 aqueous solution (0.1 ml) was added thereto, and the mixture was again reacted for 5 minutes. Then, 5 ml of 20% acetic acid aqueous solution was added to terminate the reaction. Absorbance was measured at 405 nm and $IC_{50}$ was determined by the method described above.

Assay For Inhibitory Activity Against Urokinase

An aqueous solution (0.1 ml) of 0.1 ml of the inhibitor was added to 0.3 ml of buffer (150 mM sodium chloride aqueous solution containing 50 mM Tris, pH 8.20) and the mixture was heated for 5 minutes. Thereafter 0.1 ml of urokinase solution (containing 50 mM Tris, 150 mM sodium chloride aqueous solution and 0.1% BSA, pH 8.20) was added thereto, and the mixture was reacted for 5 minutes. Furthermore, 10 mM MUK-34 aqueous solution (0.1 ml) was added thereto, and the mixture was reacted for 5 minutes. Then 10% acetic acid aqueous solution (2.0 ml) was added to the mixture to terminate the reaction. Absorbance was measured at 405 nm and $IC_{50}$ was determined by the method described above.

TABLE 1

Known Compounds

| No. | Compound | Structural Formula |
|---|---|---|
| A1 | Leupeptin | Ac—L—Leu—L—Leu—L—Arg—H.½H$_2$SO$_4$ |
| A2 | fPA | H—D—Phe—L—Pro—L—Arg—H.H$_2$SO$_4$ |
| A3 | FOY | $C_2H_5OC-\bigcirc-OC(CH_2)_5-NC(NH)(NH_2)H \cdot CH_3SO_3H$ |

TABLE 2

$IC_{50}$ (× 10$^{-7}$ M) of Known Compounds

| Compound No. | Plasmin | Thrombin | Trypsin | Kallikrein | Factor Xa | Urokinase |
|---|---|---|---|---|---|---|
| A1 | 200 | 5900 | 7.8 | 69 | 140 | 10$^3$< |
| A2 | 190 | 0.25 | 0.69 | 310 | 250 | 420 |
| A3 | 400 | 320 | 19 | 45 | 130 | 11 |

Leupeptin (acetyl-L-leucyl-L-leucyl-argininal) and fPA (D-phenylalanyl-L-prolyl-L-argininal) which are structurally similar to the compounds of the present invention inhibit trypsin, and trypsin and thrombin, respectively, but do not strongly inhibit other plasmins, kallikrein, factor Xa and urokinase. On the other hand, some compounds of the present invention are characterized by strongly inhibiting many trypsin-like serine proteases such as plasmin, thrombin, trypsin, kallikrein, factor Xa, urokinase, etc., as described above. Therefore, the compounds of the present invention can inhibit a variety of trypsin-like serine proteases in vivo and because of their remarkable pharmaceutical effects, these compounds can be expected as novel protease inhibitors.

TABLE 3

$IC_{50}(\times 10^{-7}M)$ of $A-NCH(H)-C(=O)-Pro-Arg-H.Y$ where the NCH bears $(CH_2)_4-NHB$

| No. | A | B | Y | Plasmin | Thrombin | Trypsin | Kallikrein | Factor Xa | Urokinase |
|---|---|---|---|---|---|---|---|---|---|
| 1 | H | —SO$_2$—⟨◯⟩—Me | H$_2$SO$_4$ | 15 | 3.0 | 0.48 | 0.29 | 65 | 350 |
| 3 | H | —SO$_2$-naphthyl | H$_2$SO$_4$ | 5.5 | 2.0 | 0.32 | 0.40 | 35 | 220 |
| 5 | H | —SO$_2$Et | H$_2$SO$_4$ | 63 | 13 | 0.65 | 54 | 180 | 810 |

TABLE 3-continued $IC_{50}(\times 10^{-7}M)$ of
$$A-\underset{H}{NCH}-\underset{\underset{O}{\|}}{\overset{\overset{NHB}{|}}{\overset{|}{\underset{|}{(CH_2)_4}}}}{C}-Pro-Arg-H.Y$$

| No. | A | B | Y | Plasmin | Thrombin | Trypsin | Kallikrein | Factor Xa | Urokinase |
|---|---|---|---|---|---|---|---|---|---|
| 7 | H | -C(=O)-C₆H₄-CH₃ | H₂SO₄ | 10 | 3.5 | 0.11 | 2.0 | 48 | 79 |
| 9 | H | -C(=O)CH₂-C₆H₅ | H₂SO₄ | 26 | 9.3 | 0.68 | 2.0 | 150 | 830 |
| 10 | H | -C(=O)CH₃ | H₂SO₄ | 43 | 3.3 | 0.60 | 40 | 41 | 400 |
| 15 | iBuOC(=O)- | -SO₂-C₆H₄-Me | ½H₂SO₄ | 0.59 | 4.4 | 0.22 | 0.37 | 3.5 | 14 |
| 17 | -SO₂-C₆H₄-Me | -SO₂-C₆H₄-Me | ½H₂SO₄ | 0.60 | 6.3 | 0.35 | 0.38 | 4.6 | 35 |
| 20 | 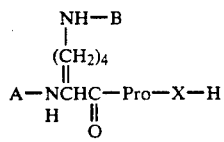 | -SO₂-C₆H₄-Me | ½H₂SO₄ | 2.5 | 12 | 0.43 | 1.7 | 11 | 66 |

What is claimed is:

1. A tripeptide derivative represented by the following formula:

$$A-\underset{H}{NCHC}-Pro-X-H$$
with $(CH_2)_4-NH-B$ side chain wherein A represents a hydrogen atom, a $C_{1-6}$-alkyloxycarbonyl group, a benzenesulfonyl group, a naphthalenesulfonyl group, a $C_{1-6}$-alkyl-substituted benzenesulfonyl group, a $C_{1-4}$-alkyl-substituted naphthalenesulfonyl group, or a $C_{2-10}$ acyl group; B represents a benzenesulfonyl group, a naphthalenesulfonyl group, a $C_{1-6}$-alkyl-substituted benzenesulfonyl group, a $C_{1-6}$-alkyl-substituted naphthalenesulfonyl group, a quinolinesulfonyl group, a pyridinesulfonyl group, a $C_{1-6}$-alkanesulfonyl group, a benzoyl group, a naphthoyl group, a $C_{1-6}$-substituted benzoyl group, a $C_{1-6}$-alkyl-substituted naphthoyl group, a $C_{2-10}$ acyl group, a phenyl-substituted $C_{2-10}$-acyl group, a $C_{5-7}$-cycloalkanecarbonyl group, or a $C_{1-6}$-alkyl substituted $C_{5-7}$ cycloalkanecarbonyl group; Pro represents L-proline residue; and X represents L-, D-, or DL-arginine residue, or an acid addition salt; and wherein the lysine residue is in the D-form.

* * * * *